United States Patent [19]

Miura et al.

[11] Patent Number: 5,022,486

[45] Date of Patent: Jun. 11, 1991

[54] SOUND REPRODUCING APPARATUS

[75] Inventors: Masayoshi Miura, Chiba; Kiyofumi Inanaga; Hiroyuki Sogawa, both of Kanagawa; Yasuhiro Iida, Tokyo, all of Japan

[73] Assignee: Sony Corporation, Tokyo, Japan

[21] Appl. No.: 409,929

[22] Filed: Sep. 20, 1989

[51] Int. Cl.[5] .................................... A61B 7/02

[52] U.S. Cl. .................................... 181/132; 181/148; 381/154; 381/187

[58] Field of Search ............... 181/130, 137, 129, 148, 181/132; 381/25, 68.6, 74, 154, 158, 169, 183, 187

[56] References Cited

U.S. PATENT DOCUMENTS

| | | | |
|---|---|---|---|
| 3,863,028 | 1/1975 | Fixler | 381/158 X |
| 4,110,583 | 8/1978 | Lepper | 381/158 |
| 4,173,715 | 11/1979 | Gosman | 181/129 X |
| 4,251,686 | 2/1981 | Sokolich | 381/154 X |

*Primary Examiner*—Brian W. Brown

*Attorney, Agent, or Firm*—Hill, Van Santen, Steadman & Simpson

[57] ABSTRACT

A sound reproducing apparatus is provided formed of an acoustic tube having first and second opposite ends, and having substantially a same inside diameter as that of an external acoustic meatus of the user who is wearing the sound reproducing apparatus. A loudspeaker unit is mounted to the acoustic tube intermediate the first and second ends such that a sound radiating surface thereof is directed to one side of the acoustic tube. The acoustic tube has at its first end an auricular attachment which is received at the external acoustic meatus. A second end is formed as a non-sound-reflecting end. The sound reproducing apparatus may also be adapted to have two loudspeaker units mounted to one or more acoustic tubes, respectively, and two auricular attachment sections may be provided, one for each ear. Left and right channel acoustical signals may be respectively input to the respective first and second loudspeaker units for stereo operation.

53 Claims, 17 Drawing Sheets

SOUND REPRODUCING APPARATUS

BACKGROUND OF THE INVENTION

Related Art Statement

This invention relates to a sound reproducing apparatus in which the reproduced sound from a loudspeaker unit is heard via an acoustic tube attached to an auricle. More particularly, it relates to a sound reproducing apparatus in which the reproduced sound from the loudspeaker unit is radiated into an acoustic tube having one end arranged as an auricular attachment section and the other end arranged as a non sound-reflecting end, and in which the reproduced sound is heard by way of the acoustic tube.

Various types of sound reproducing apparatus, are known such as the earphone or headphone type apparatus, in which the reproduced sound is heard with a loudspeaker unit attached to the listener's auricle.

When the reproduced sound is heard with the sound reproducing apparatus now in extensive use, such as an earphone, the reproduced sound radiated from the loudspeaker unit may be heard as the reproduced sound radiated from the loudspeaker unit is radiated from an earphone casing accommodating the loudspeaker unit through the external acoustic meatus to set the tympanic membrane into oscillations.

In the above earphone, the reproduced sound reaching the tympanic membrane tends to be reflected thereat and to exit the auricle by way of the external acoustic meatus. However, in the conventional earphones, the earphone casing is attached to the auricle as it encloses the external acoustic meatus, so that the reflected sound tending to exit the auricle is reflected by the casing or the loudspeaker unit therein so as to be radiated again into the external acoustic meatus to travel towards the tympanic membrane.

Hence, in the above described conventional earphones, the sound directly radiated from the loudspeaker unit towards the tympanic membrane and the sound once reflected by the tympanic membrane and again reflected at the earphone casing or at the loudspeaker unit are heard by the listener.

When the reproduced sound directly radiated towards the tympanic membrane and the sound reflected by the tympanic membrane are temporally spaced apart by a period not more than several hundred microseconds, the sounds are heard as if the sound source is within the user's head so as to impart a "fixed" or "oppressed" feeling to the listener.

In order to prevent the sound once reflected by the tympanic membrane from being reflected again by the earphone housing, there is proposed an earphone in which a central portion of a diaphragm of a loudspeaker unit provided facing towards the external acoustic meatus of the auricle is removed so that the reproduced sound is radiated only from the periphery of the diaphragm. In such case, the sound directly reflected onto the earphone housing may be reduced, while the region of the diaphragm set into oscillations by the reflected sound may be lessened, resulting in a reduced amount of the reflected sound re-radiated towards the diaphragm, and improved sound reproducing characteristics.

However, when the sound source at the loudspeaker unit side is seen from the external acoustic meatus, the acoustic impedance at the entrance to the external acoustic meatus differs from that within the external acoustic meatus resulting again in sound reflection at an area between the earphone casing and the entrance to the external acoustic meatus, with the reflected sound being re-directed towards the tympanic membrane Thus the above mentioned "fixed" or "oppressed" feeling cannot be avoided There is also proposed an earphone in which the sound reflection by the earphone casing or the like is avoided by reverse filter techniques.

However, the reverse filter techniques present disadvantages in that they are not universally applicable since the acoustic impedance of the tympanic membrane is not the same for individual users and hence the reverse filter needs to be tailored to each user.

Thus there is devised a sound reproducing apparatus in which, in order to prevent sound reflection at the loudspeaker unit or the earphone casing on the sound source side as the sound source side is viewed from the entrance to the external acoustic meatus, or sound reflection caused by impedance changes at the entrance to the external acoustic meatus, the reproduced sound radiated from the loudspeaker unit is transmitted to the auricle by way of an acoustic tube.

Meanwhile, in this type of the sound reproducing apparatus employing an acoustic tube, a loudspeaker unit is provided on one lateral side of the acoustic tube. As such a loudspeaker unit, a loudspeaker having a diaphragm is generally employed.

However, in general, the acoustic impedance of a diaphragm employed in a diaphragm type loudspeaker is lower than that within the inside of the acoustic tube. On the other hand, it is difficult to attach the diaphragm type loudspeaker to the tube, with the sound radiating surface thereof directed to the inside of the tube, without changing the inside diameter of the acoustic tube. Therefore, when the loudspeaker unit is simply mounted on one side of the acoustic tube, sound reflection occurs at the site of the diaphragm of the loudspeaker unit.

Objects and Summary of the Invention

It is an object of the present invention to provide a sound reproducing apparatus in which the reproduced sound radiated from the loudspeaker unit is heard by way of an acoustic tube attached to the listener's auricle.

It is another object of the present invention to provide a sound reproducing apparatus in which the sound radiated from the loudspeaker unit and introduced into the external acoustic meatus by way of the acoustic tube to reach the tympanic membrane so as to be reflected by the tympanic membrane may be prevented from being re-reflected by the diaphragm of the loudspeaker unit, or due to changes in the acoustic impedance at the entrance to the external acoustic meatus.

It is a further object of the present invention to provide a sound reproducing apparatus in which the acoustic impedance of the acoustic tube is rendered constant and the sound reflected from the external acoustic meatus may be prevented from being re-reflected within the acoustic tube.

It is a further object of the present invention to provide a sound reproducing apparatus which can be attached to the auricle with a good wearing feeling.

It is a further object of the present invention to provide a sound reproducing apparatus in which the length of the acoustic tube adapted for transmitting the reproduced sound radiated from the loudspeaker unit towards the auricle may be shortened by prompt attenuation of the reflected sound from the auricle.

It is a further object of the present invention to provide a sound reproducing apparatus in which the auricular attachment section mounted to one end of the acoustic tube may be detached and exchanged to cope with the external acoustic meatus differing from user to user.

It is a further object of the present invention to provide a sound reproducing apparatus in which the sounds from outside other than the reproduced sound may be heard even when the auricular attachment section provided at one end of the acoustic tube is attached to the auricle to stop up the external acoustic meatus.

It is a further object of the present invention to provide a sound reproducing apparatus allowing the listener to hear stereophonic sounds.

It is yet another object of the present invention to provide a sound reproducing apparatus in which, when the apparatus is designed as a stereophonic sound reproducing apparatus, the crosstalk components of the reproduced sound radiated from left and right loudspeaker units are obtained to provide for a "relaxed" listening feeling, that is, a listening feeling as if the sound source were outside of the listener's head and the listener is hearing the reflected sound from the loudspeaker units located at some distance from the listener.

According to the present invention, there is provided a sound reproducing apparatus comprising an acoustic tube having approximately the same inside diameter as that of the external acoustic meatus and a loudspeaker unit mounted on one side of the acoustic tube with its sound radiating surface directed to the inside of the tube. The acoustic tube has its one end arranged as the auricular attachment section and the other end arranged as 1 non-sound-reflecting end. According to the present invention, the acoustic tube of the sound reproducing apparatus has an inside diameter approximately equal to that of the external acoustic meatus, so that, when the sound reflected by the tympanic membrane exits the external acoustic meatus to enter the inside of the tube, the acoustic impedance is not changed. Since the other end of the tube is arranged as the non-sound-reflecting end, the sound exiting the external acoustic meatus to be re-introduced into the latter is not re-reflected at the other end of the tube towards the tympanic membrane The above and other objects, advantages and features of the present invention will become apparent from the following description especially when read in conjunction with the accompanying drawings

DESCRIPTION OF PREFERRED EMBODIMENT

An embodiment of the earphone type sound reproducing apparatus attached in use to the user's auricles according to the present invention will be explained hereinbelow in detail.

Figure 1:
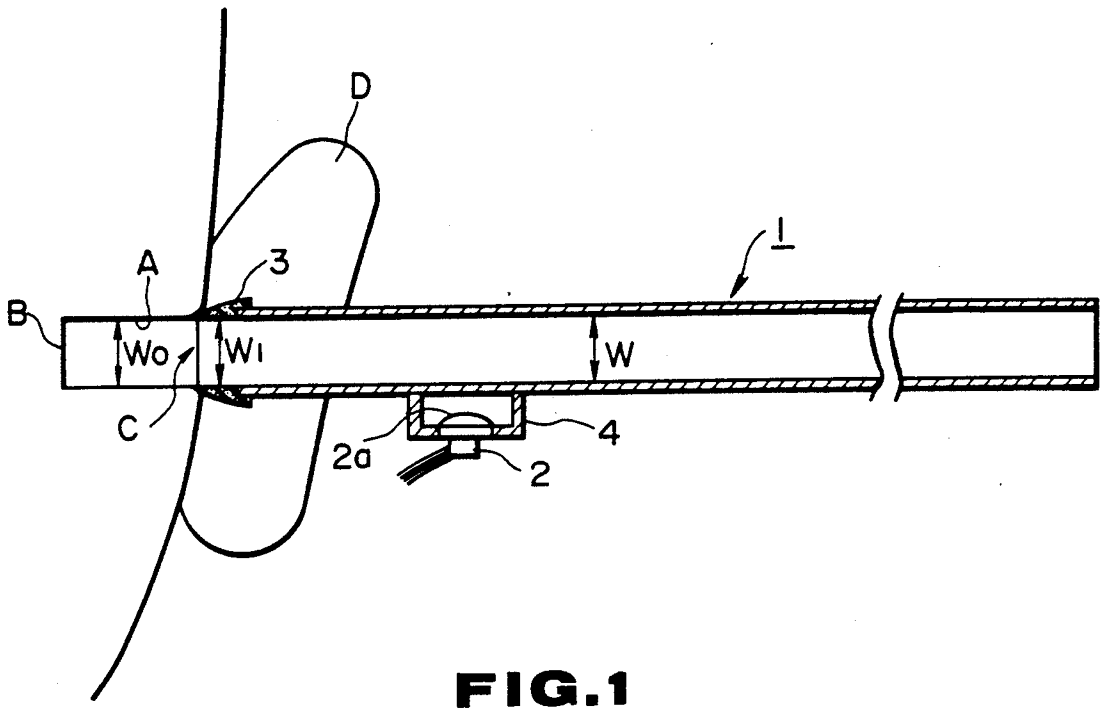
FIG. 1 is a diagrammatic cross-sectional view showing an earphone type sound reproducing apparatus according to the present invention.

As shown in FIG. 1, the sound reproducing apparatus of the present invention is mainly composed of an acoustic tube 1 and a loudspeaker unit 2 for radiating reproduced sounds propagated within this acoustic tube.

The acoustic tube 1 is formed as an elongated tubular body having an inside diameter W which is constant over its length and approximately equal to the inside diameter $W_0$ of an external acoustic meatus A. The inside of the acoustic tube 1 acts as a sound path for transmitting the reproduced sound radiated from a loudspeaker unit 2 to the auricla. By having the inside diameter W of the acoustic tube 1 approximately equal to the inside diameter $W_0$ of the acoustic meatus A, the acoustic impedance of the acoustic tube 1 may be made approximately equal to that of the external acoustic meatus A. With the acoustic impedance of the acoustic tube approximately equal to that of the external acoustic meatus A, it becomes possible to prevent sound reflections due to changes in the acoustic impedance otherwise caused when the sound reflected by a tympanic membrane B exits to the outside via an entrance C to the external acoustic meatus A, as well as to prevent the reflected sound from being re-introduced into the external acoustic meatus A. Hence it suffices to select the inside diameter W of the acoustic tube 1 to be about equal to the mean inside diameter of the external acoustic meatus A. The mean value of the inside diameter $W_0$ of the external acoustic meatus A of an adult is said to be about 7.5 mm. Therefore, by setting the inside diameter W of the acoustic tube 1 so as to be 6 to 9 mm, it becomes possible to reduce the difference in cross-sectional area between the acoustic tube L and the entrance C to the external acoustic meatus A to eliminate sound reflection to prevent generation of standing waves to and thus prevent the reflected sound from reaching the tympanic membrane B so as to produce satisfactory acoustic characteristics.

The acoustic tube 1 is fitted with an auricle attachment member 3 for attaching the one side of the tube to the entrance C to the external acoustic meatus A. The attachment member 3 is formed of resilient synthetic resin or rubber to improve the feeling of attachment to the auricle D. It is noted that this attachment member 3 also has an inside diameter $W_1$ equal to the inside diameter W of the acoustic tube 1 to prevent the acoustic impedance properties from being changed in the acoustic tube 1.

The other end extremity of the acoustic tube 1 is designed so as to be exempt from sound reflection. That is, the acoustic tube 1 is open at the other end opposite to the side of attachment to the entrance A, and is formed as an elongated tubular body.

With the acoustic tube 1 being of the same inside diameter W for its overall length and being open at its other end, sound reflection may be prevented from occurring at the other end. Even in the case of occurrence of some sound reflection, the phenomena of stereotropism within the head may be inhibited by setting the delay in the propagation time to the auricle of the reflected sound with respect to the reproduced sound directly radiated from the loudspeaker unit 2.

That is, the acoustic impedance of the acoustic tube 1 as viewed from the external acoustic meatus A can be matched to that of the external acoustic meatus A, so that, as a principle, sound reflection does not occur at the terminal end of the acoustic tube 1. Therefore, the sound reflected by the tympanic membrane B is not reflected back at the side of an earphone device so as to re-enter the tympanic membrane B. Hence, it becomes possible to prevent the occurrence of the phenomenon of stereotropism in the head, that is, the phenomena in which the sound image becomes fixed in the hearer's head while the hearer is listening to the reproduced sound.

Figure 2A:
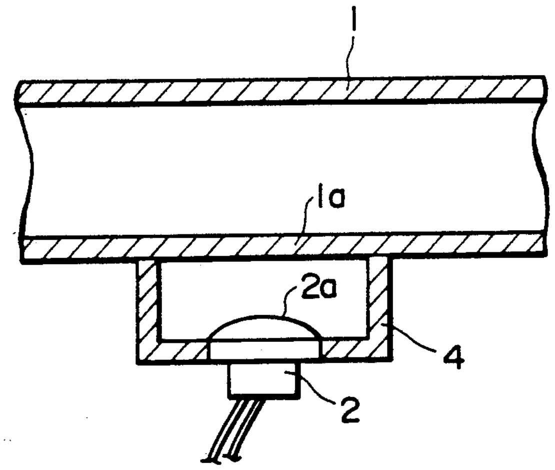
FIG. 2A is an enlarged longitudinal cross-sectional view showing essential portions of a loudspeaker mounting section.
Figure 2B:
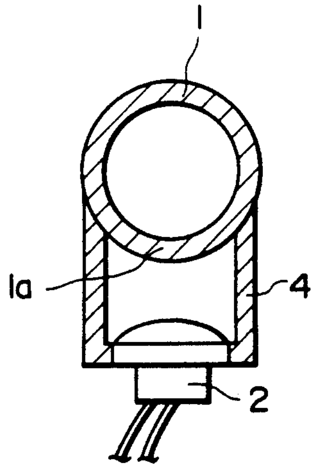
FIG. 2B is an enlarged transverse cross-sectional view showing essential parts thereof.

The above described acoustic tube 1 is fitted with the loudspeaker unit 2 for radiating the reproduced sound propagated to the auricle via this acoustic tube 1. The loudspeaker unit 2 herein employed is of the dynamic type. As shown in FIGS. 2A and 2B, this loudspeaker unit 2 is attached to the acoustic tube 1 via a housing 4 provided about the outer periphery of the acoustic tube 1. The loudspeaker unit 2 is fitted in a mounting hole 4a in the housing 4, with its sound radiating surface 2a facing toward the interior of the tube 1. With the loudspeaker unit 2 mounted in this manner, part of the acoustic tube 1 facing towards the sound radiating surface 2a of the loudspeaker unit 2 within the housing 4 is excited into vibrations under the pressure of the reproduced sound radiated from the loudspeaker unit 2 upon actuation of the loudspeaker unit 2. As a result, the reproduced sound from the loudspeaker unit 2 is propagated into the sound tube 1.

By attaching the loudspeaker unit 2 on the outer periphery of the acoustic tube 1, as described hereinabove, a uniform inside diameter W of the acoustic tube 1 may be maintained along its overall length, so that a uniform acoustic impedance may be assured for the sound reflected from the tympanic membrane B. This results in prevention of re reflection of the reflected sound.

Figure 3A:
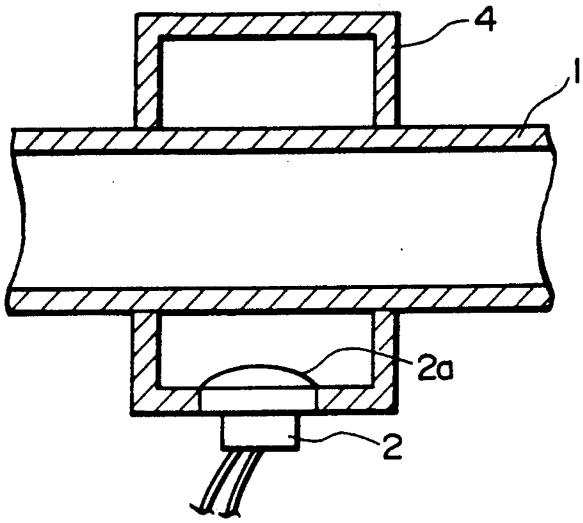
FIG. 3A is an enlarged longitudinal cross-sectional view showing essential parts of another example of the loudspeaker mounting section.
Figure 3B:
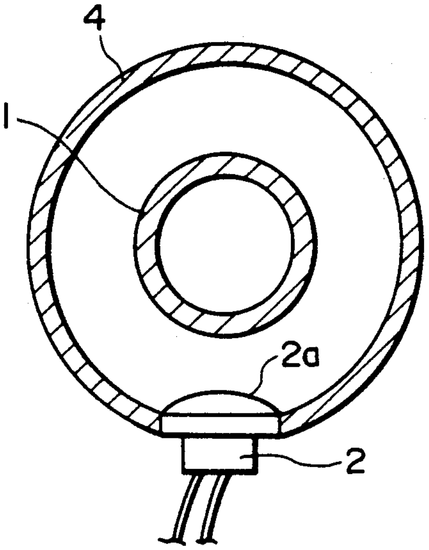
FIG. 3B is an enlarged transverse cross-section view showing essential parts thereof.

It is noted that, although a portion 1a of the acoustic tube 1 facing toward the loudspeaker unit 2 in the housing 4 may be formed of the same material as that of the remaining portion of the tube 1, it may be formed of a material exhibiting higher oscillation properties within the range of not changing acoustic impedances within the acoustic tube 1, in order that the reproduced sound may be propagated more accurately within the acoustic tube 1. The housing 4 may also be formed for surrounding the overall outer periphery of the acoustic tube 1, as shown in FIGS. 3A and 3B, instead of being formed on only a portion of the outer periphery of the tube 1.

Figure 4A:
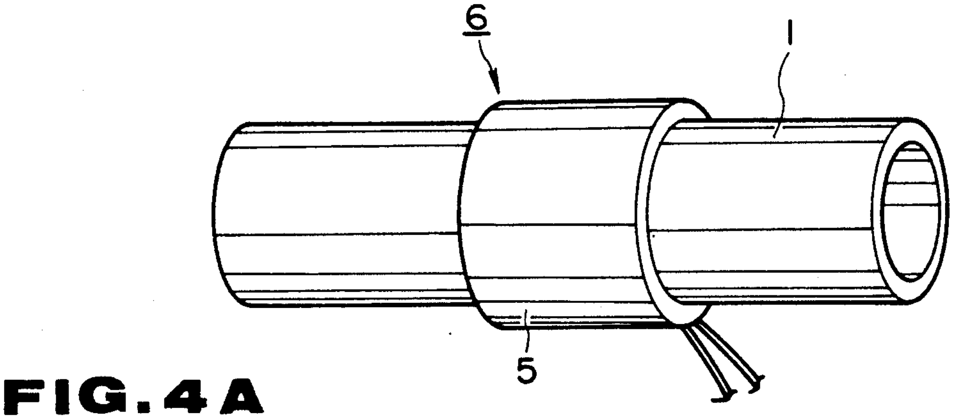
FIG. 4A is an enlarged perspective view showing an example of a loudspeaker unit employing a piezoelectric element.
Figure 4B:
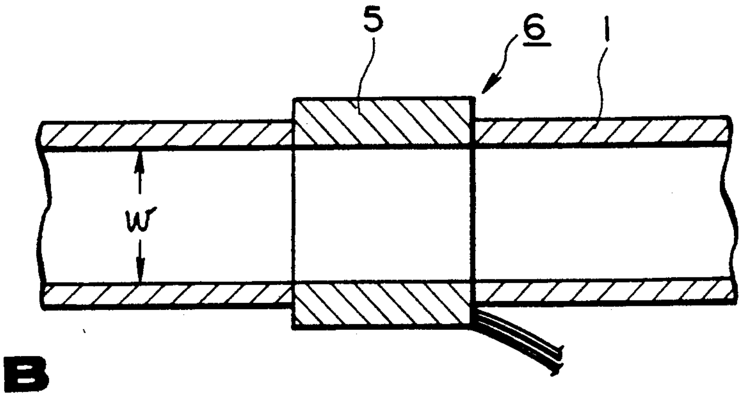
FIG. 4B is an enlarged transverse cross-sectional view showing essential parts thereof
Figure 5:
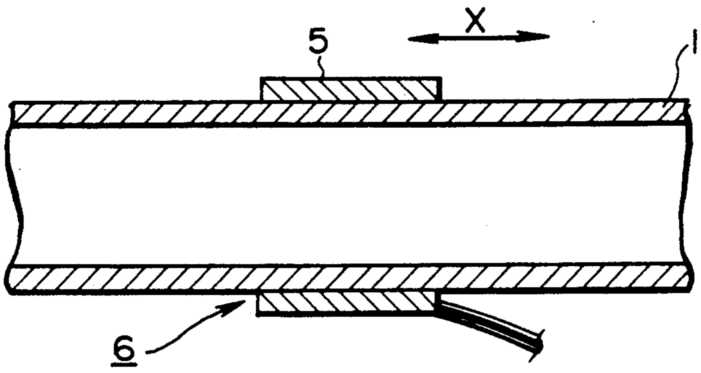
FIG. 5 is an enlarged longitudinal cross-sectional view showing essential parts of another example of a loudspeaker unit employing a piezoelectric element

Although the loudspeaker unit 2 in the above described embodiment is of the dynamic type, the loudspeaker unit 6 may also make use of a piezoelectric element 5, as shown in FIGS. 4A and 4B. The piezoelectric element 5 of the loudspeaker unit 6 is formed as a cylinder having the same inside diameter as the inside diameter W of the acoustic tube 1. As shown in FIG. 4B, the piezoelectric element 5 is connected to an intermediate portion of the acoustic tube 1 so that the element 5 forms a part of the tube 1. By driving the piezoelectric element 5 with driving currents corresponding to the piezoelectric element 5, it becomes possible to radiate the desired reproduced sound into the interior of the acoustic tube 1.

Meanwhile, the piezoelectric element 5 is formed as a cylinder having the same diameter as the inside diameter W of the acoustic tube 1, so that the inside diameter of the acoustic tube 1 is not changed, and hence the provision of the piezoelectric element 5 does not result in changing the acoustic impedance.

The piezoelectric element 5 may be formed as a cylinder sized to fit tightly on the outer periphery of the acoustic tube 1, such that it may be fitted on the outer periphery of the tube 1. The piezoelectric element 5, fitted in this manner, causes the tube 1 to be excited directly into oscillations to radiate the reproduced sound within the acoustic tube 1. Assuming that the piezoelectric element 5 is movable along the axial direction x of the acoustic tube the sense of the distance of the sound source from the user's head can be changed as desired.

Figure 6:
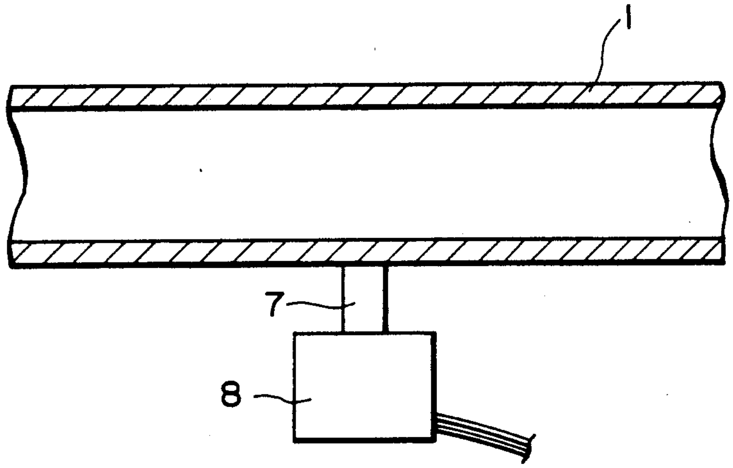
FIG. 6 is an enlarged longitudinal cross-sectional view showing essential parts of another example of a mounting state of the loudspeaker unit to an acoustic tube.

In the above described illustrative embodiment, part of the acoustic tube 1 may be directly forced into oscillations by the piezoelectric element 5 forming the loudspeaker unit 2 or 6 for radiating the reproduced sound into the interior of the tube 1. The acoustic oscillations of the speaker unit 8 may also be transmitted to the tube 1 via an oscillation transmitting section 7, as shown in FIG. 6. That is, the sound reproducing apparatus shown in FIG. 6 is so designed and constructed that the oscillation transmitting section 7 adapted for transmitting acoustic oscillations from the speaker unit 8 is directly connected to the outer periphery of the acoustic tube 1, and that the acoustic tube 1 is excited into oscillations for radiating the reproduced sound into the inside of the acoustic tube 1.

Figure 7:
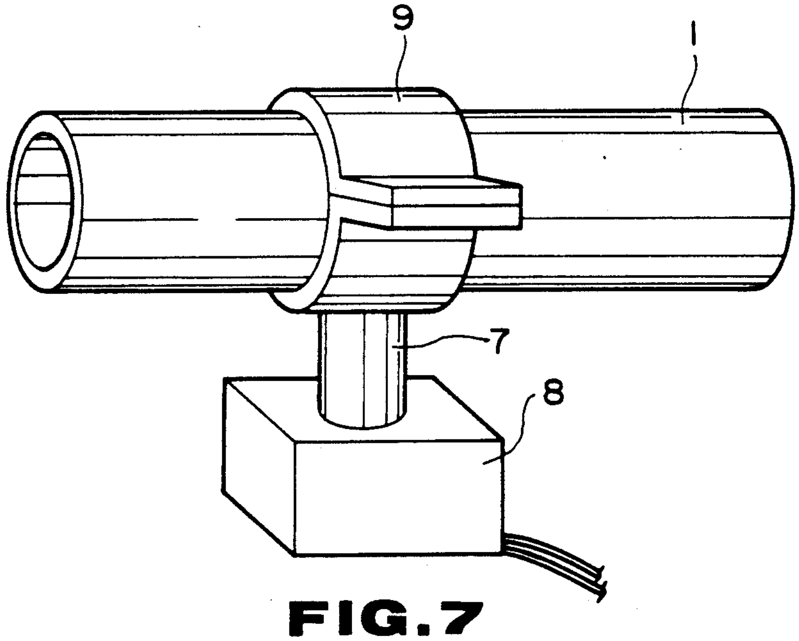
FIG. 7 is an enlarged perspective view showing still another example of the mounting state of the loudspeaker unit to an acoustic tube.

Meanwhile, the speaker unit 8 may be designed similarly to the ordinary dynamic type speaker in such a manner that the oscillation transmitting section 7 is driven for causing oscillations of the acoustic tube 1. The speaker unit 8 may also be mounted to the acoustic tube 1 by the medium of an attachment member 9, as shown in FIG. 7, and the attachment position of this attachment member 9 with respect to the acoustic tube 1 and hence the position of sound generation in the acoustic tube 1 may be made variable to render the sense of the distance of the sound source from the user's head similarly variable.

In the sound reproducing apparatus employing the dynamic type loudspeaker unit 2, as shown in FIG. 1 the housing 4 is provided on the outer periphery of the acoustic tube 1, the loudspeaker unit 2 is attached to this housing 4, the reproduced sound is radiated into the inside of this housing 4, and part of the acoustic tube 1 is excited into oscillations by the reproduced sound radiated into the inside of the housing 4, with the reproduced sound being propagated into the inside of the acoustic tube 1. The above described sound reproducing apparatus making use of the galvanic type loudspeaker unit 2 may also be so designed and constructed that the reproduced sound radiated from the loudspeaker unit 2 will be radiated directly into the inside of the acoustic tube 1 so as to be propagated towards the auricle.

Figure 8:
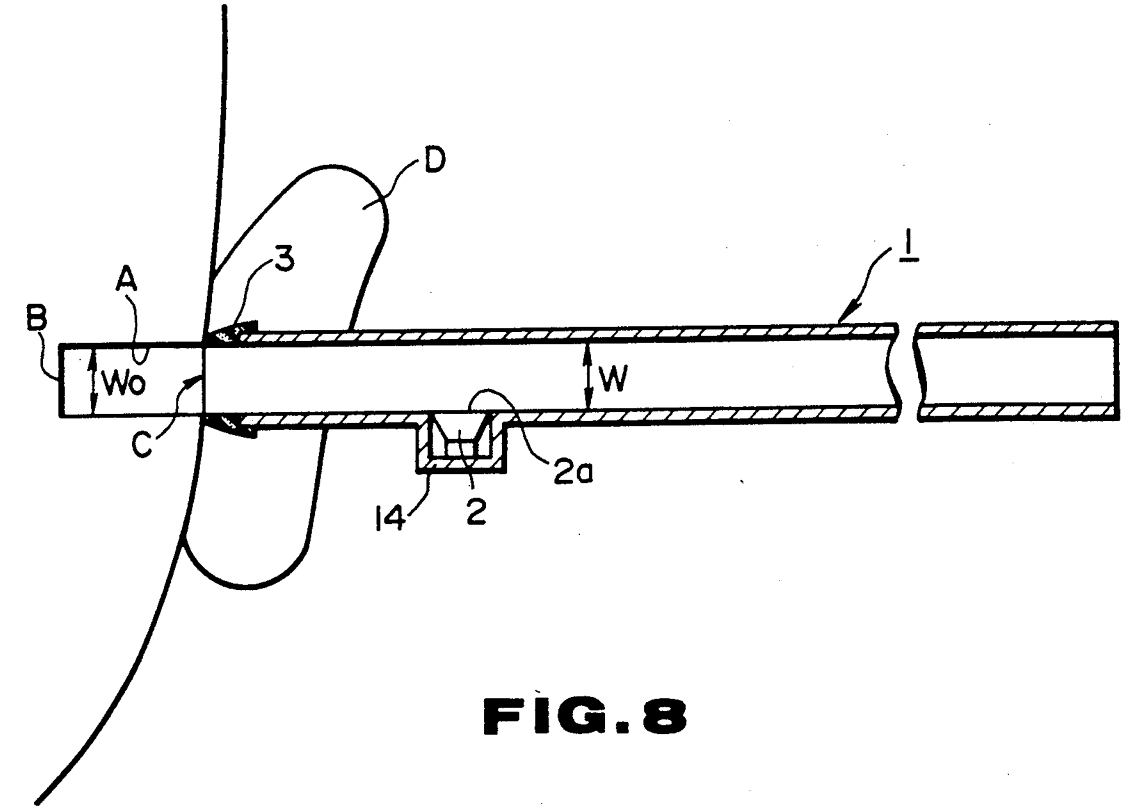
FIG. 8 a schematic cross-sectional view showing a sound reproducing apparatus in which the loudspeaker unit faces toward the inside of the acoustic tube.
Figure 9:
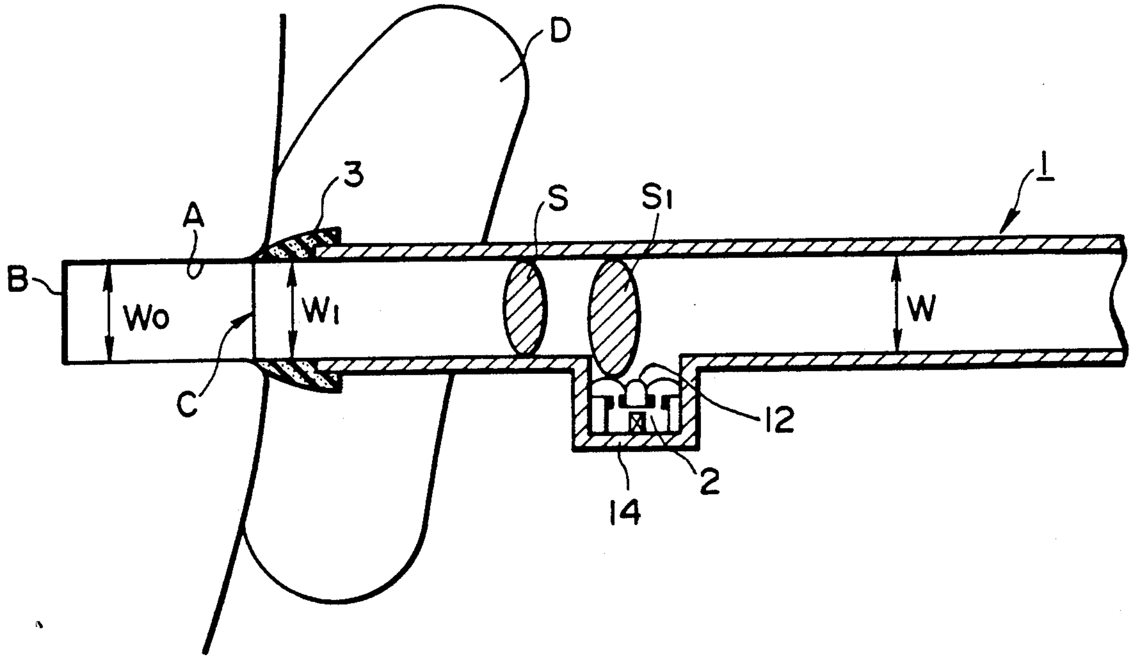
FIG. 9 is an enlarged cross-sectional view showing essential parts of an example of mounting a loudspeaker unit to an acoustic tube.

FIG. 8 shows an arrangement in which the reproduced sound radiated from the dynamic type loudspeaker unit 2 is radiated directly into the acoustic tube 1. The sound reproducing apparatus shown in FIG. 8 is so designed and constructed that part of the acoustic tube 1 is bulged out to define a loudspeaker unit containing section 14 in which the dynamic type loudspeaker unit 2 is accommodated. This loudspeaker unit 2 is mounted with the sound radiating surface 2a facing to the inside of the acoustic tube 1. The loudspeaker unit 2 is preferably mounted so as not to render the inside diameter W of the acoustic tube 1 variable to prevent the acoustic impedance of the acoustic tube 1 from being disturbed.

That is, when the loudspeaker unit 2 is mounted to the acoustic tube 1, a diaphragm 12 as the sound radiating surface 2a of the loudspeaker unit 2 is positioned towards the containing section 14 for the loudspeaker unit 2, and the cross-sectional area S of the acoustic tube 1 is enlarged at the loudspeaker unit containing section 14. That is, when the cross-sectional area $S_1$ of the loudspeaker unit containing section 14 is enlarged, and the inside diameter of the acoustic tube 1 is made significantly variable, the acoustic impedance within the acoustic tube 1 is made variable. As a result, sound reflection occurs at an area between the entrance to the external acoustic meatus and the loudspeaker unit containing section, with the reflected sound returning to the tympanic membrane. Hence, there is the risk of the sound image being fixed in the user's head, a phenomenon occurring above all during listening with an earphone.

Figure 10:
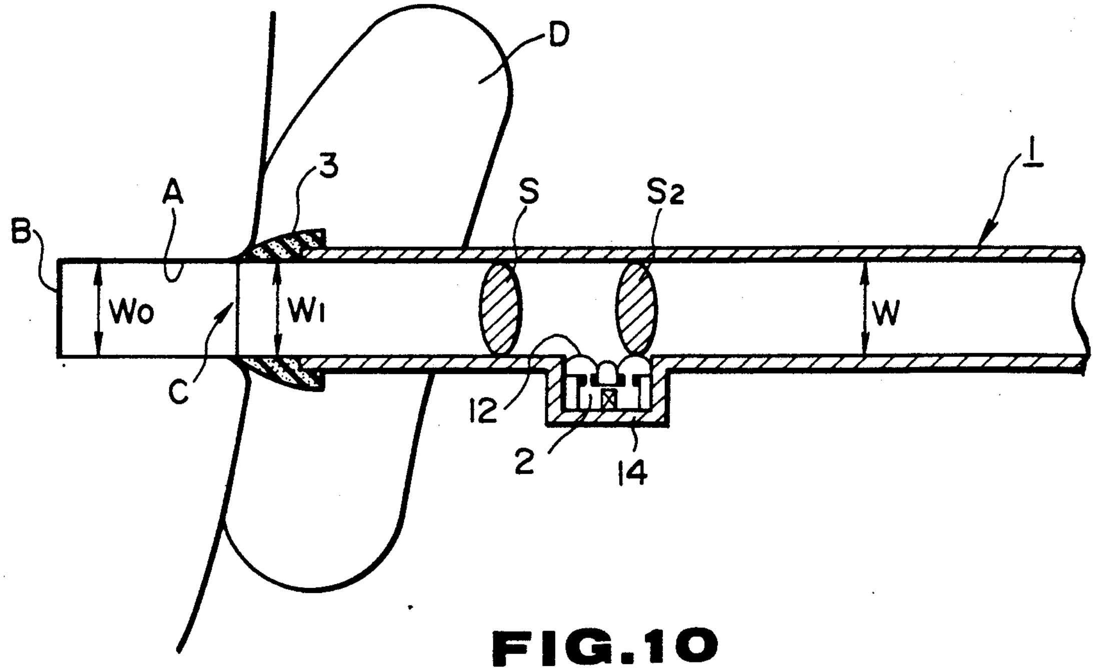
FIG. 10 is an enlarged cross-sectional view showing essential parts of an example of mounting the loudspeaker unit in a desirable state to the acoustic tube.

It is noted that the loudspeaker unit 2 mounted to the acoustic tube 1 is mounted with the diaphragm 12 extending parallel to the lateral side of the acoustic tube 1, as shown in FIG. 10. Preferably, the cross-sectional area S of the acoustic tube 1 is not rendered variable at the loudspeaker unit containing section 14, and the cross-sectional area $S_2$ of the loudspeaker unit containing section 14 becomes equal to the cross-sectional area S of the acoustic tube 1. By so doing, the acoustic impedance within the acoustic tube 1 may be rendered constant.

In the foregoing embodiments, the sound reproducing apparatus according to the present invention is a monoaural type earphone attached to one ear.

However, the sound reproducing apparatus according to the present invention is not limited to the foregoing embodiments, but may be arranged as a stereophonic type sound reproducing apparatus by providing two such earphones for left and right ears.

Figure 11:
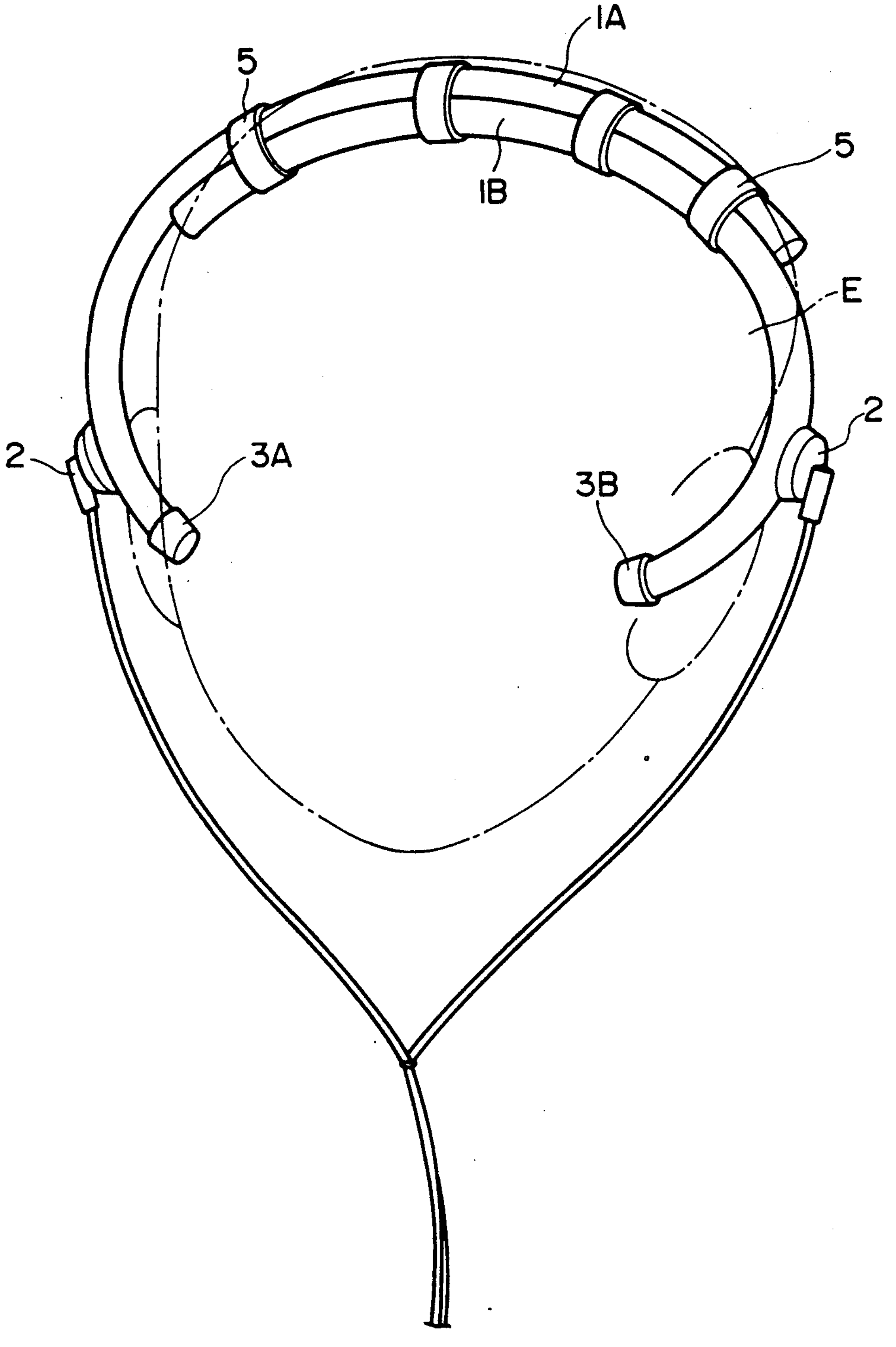
FIG. 11 is a schematic perspective view showing an example of a sound reproducing apparatus adapted for stereophonic reproduction

Referring to FIG. 11, for forming the sound reproducing apparatus shown in this figure, a left channel acoustic tube 1A and a right channel acoustic tube 1B are provided for stereophonic reproduction. These acoustic tubes 1A, 1B are bent to conform to the profile of a head E. These bent tubes 1A, 1B are partially overlapped one on the other and tightly interconnected by tightening bands 5. At this time, the acoustic tubes 1A, 1B are so mounted that the auricle attachment members 3A, 3B face to each other, so that when the tubes are attached to the head E, the auricle attachment sections 3A, 3B face the auricles.

The sound reproducing apparatus shown in FIG. 11 is attached to the head E, with the bent acoustic tubes 1A, 1B extended apart from each other, and the attachment sections 3A, 3B are thrusted onto the entrances C of the external acoustic meatus A from both sides to prevent the attachment sections 3A, 3B from disengaging from the auricles D to allow for satisfactory attachment.

The auricle attachment member provided on one end of the acoustic tube 1 is detachable, and a plurality of auricle attachment members, each having an outside diameter conforming to the diameter of the external acoustic meatus of different users are provided. These auricle attachment members are suitably selected to suit the particular user and are attached at one end of the acoustic tube 1 to form a sound reproducing apparatus that may be worn with a good attachment feeling by each user.

Several specific embodiments of the sound reproducing apparatus will be given hereafter.

The sound reproducing apparatus has an acoustic tube 21 which is constructed similarly to the acoustic tube of the preceding embodiment. This acoustic tube 21 is formed as an elongated tube having an inside diameter W which is uniform along its overall length and is about equal to the inside diameter $W_0$ of the external acoustic meatus A of the auricle.

A loudspeaker unit 22 is mounted on the side of the acoustic tube 21. This loudspeaker unit 22 is mounted to the acoustic tube 21 with a sound radiating surface 22*a* facing toward the inside of the acoustic tube 21. Preferably, the loudspeaker unit 22 is mounted so as not to render the inside diameter W of the acoustic tube 21 variable to prevent the acoustic impedance of the acoustic tube 21 from being disturbed.

For mounting the loudspeaker unit 22 to the acoustic tube 21, the loudspeaker unit may be contained in a housing which in turn is mounted to the acoustic tube 21, or alternatively, the loudspeaker unit may be contained in a speaker unit containing section, which in turn is mounted to the acoustic tube 21.

Figure 12:
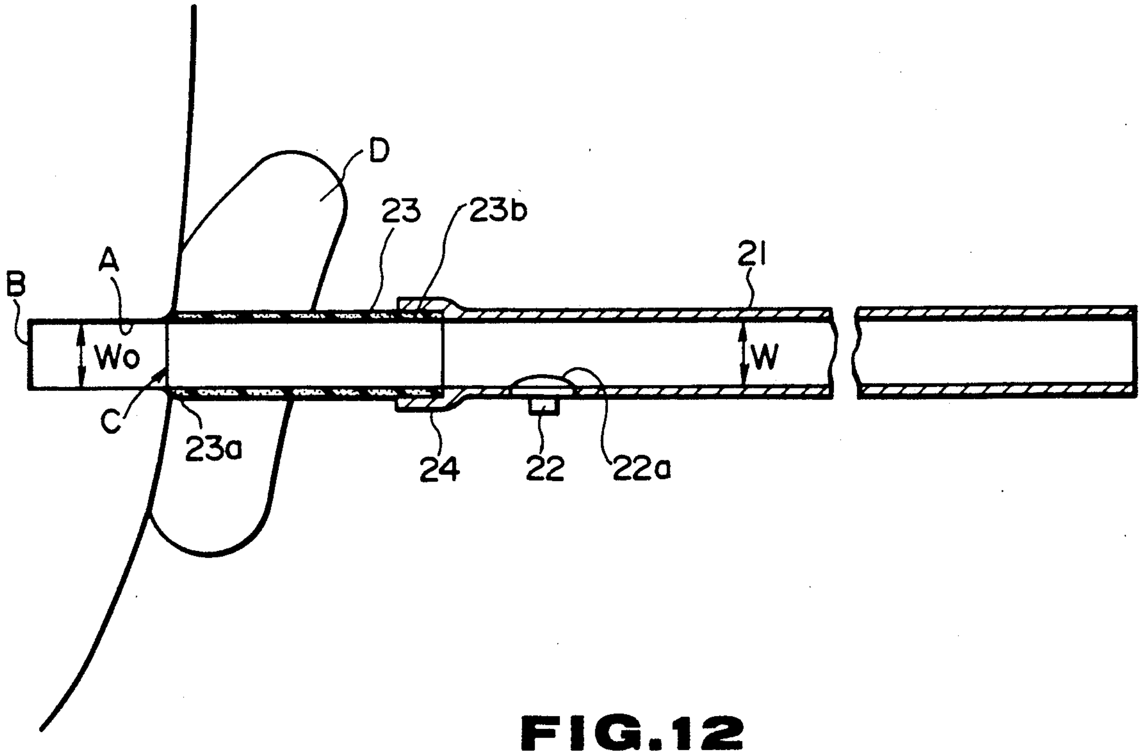
FIG. 12 is a cross-sectional view showing a sound reproducing apparatus in which the auricular attachment member is detachably mounted to the acoustic tube.

An auriclar attachment member 23, attached to an entrance C of an external acoustic meatus A of an auricle D as shown in FIG. 12, is removably mounted to one end of the acoustic tube 21. This auricular attachment member 23 is formed of resilient synthetic resin or rubber for improving the attachment feeling to the auricle D. Meanwhile, the auriclar attachment member 23 may be attached positively to the external acoustic meatus A by abutting an auriclar attachment section 23*a* of the attachment member 23 on the perimeter of the entrance C of the external acoustic meatus A or by slightly introducing the attachment section 23*a* into the entrance C which is slightly extended apart.

It is noted that the auricle attachment member 23 is mounted to the acoustic tube 21 by fitting a fitting section 23*b* opposite the auriclar attachment section 23*a* to a mating fitting section 24 formed integrally with one end of the acoustic tube 21. The auriclar attachment member 23 may be mounted and unmounted freely since it simply has a tight fit on the acoustic tube 21.

Hence, the sound reproducing apparatus that may be worn with a good attachment feeling by any person may be provided when a plurality of different kinds of the auriclar attachment members 23 with different outside diameters are rendered available in advance and one of the members suited to the inside diameter $W_0$ of the external acoustic meatus A of a particular user is selectively used.

Several different embodiments of the auricular attachment members 23 will be explained hereinbelow.

Figure 13:
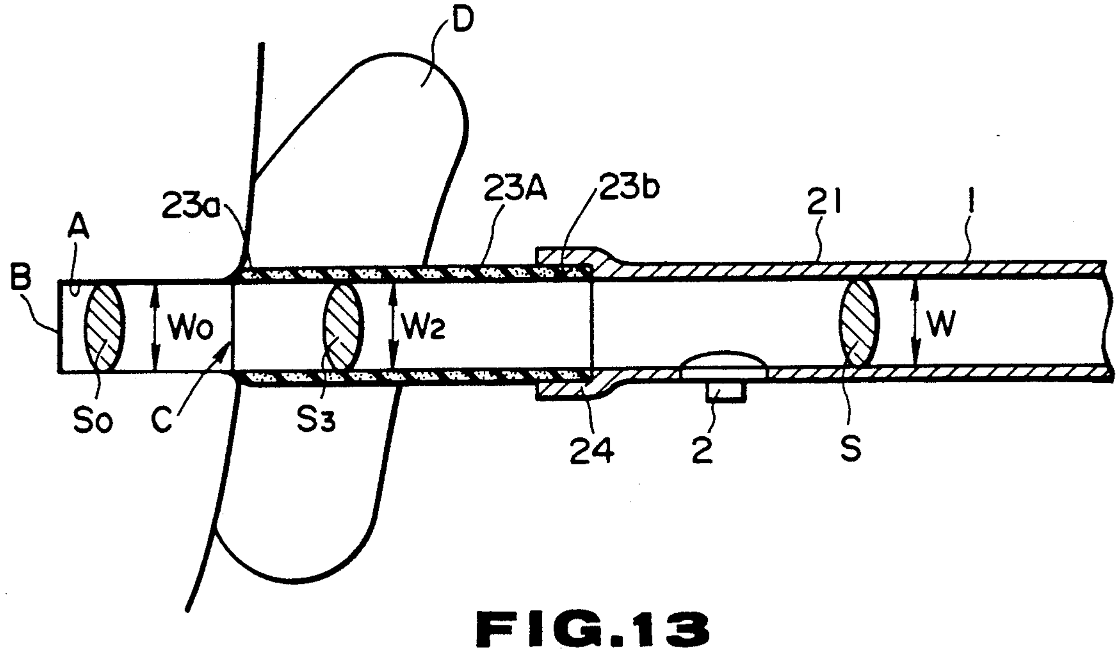
FIG. 13 is an enlarged cross-sectional view of a sound reproducing apparatus in which the standard type auricular attachment member is detachably mounted to the acoustic tube

FIG. 13 shows a first auriclar attachment member 23A of a standard size fitted to the acoustic tube 21. This first auricular attachment member 23A has its inside diameter $W_2$ approximately equal to the inside diameter W of the acoustic tube 21. The cross-sectional area $S_0$ of the external acoustic meatus A, the cross-sectional area S of the acoustic tube 21 and the cross-sectional area $S_3$ of the first auricular attachment member 23A are approximately equal to one another, so that, by setting the inside diameter $W_0$ and the cross-sectional area $S_0$ on the one hand and the inside diameter $W_1$ and the cross-sectional area $W_1$ of the first auricular attachment member 23A on the other, so as to be approximately equal to each other, the acoustic impedance characteristics are not changed when the sound reflected from the tympanic membrane B is introduced via the external acoustic meatus A into the acoustic tube 21.

Figure 14:
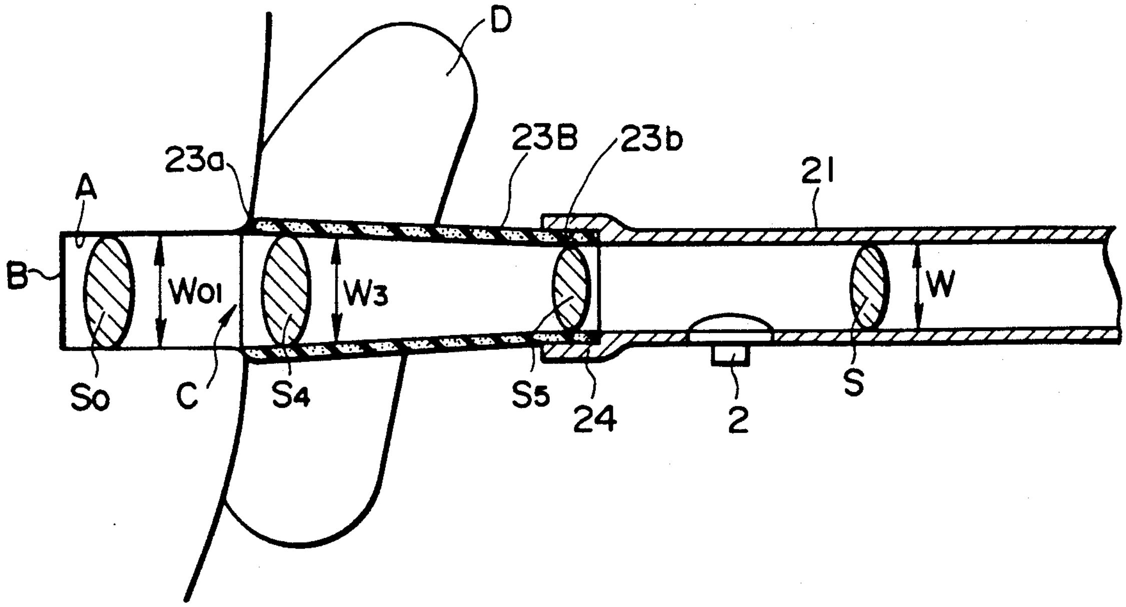
FIG. 14 is an enlarged cross-sectional view of a sound reproducing apparatus in which the large diameter auricular attachment member is detachably mounted to the acoustic tube.

FIG. 14 shows a second auricular attachment member 23B for a person whose external acoustic meatus A has an inside diameter $W_{01}$ larger than the inside diameter W of the acoustic tube 21. This second auricular attachment member 23B has the auricular attachment member 23*a* as a larger diameter section having a diameter corresponding to the larger inside diameter $W_{01}$ of the external acoustic meatus A; and the fitting section 23*b* to the acoustic tube 21 as the lesser diameter section having an inside diameter equal to the inside diameter W of the acoustic tube 21. Thus the second auricular attachment member 23B has its inside diameter $W_3$ changing gradually from the auricular attachment section 23*a* toward the fitting section 23*b*. The cross-sectional areas $S_4$ to $S_5$ from the second auricular attachment member 23B towards the fitting section 23*b* is made variable gradually and continuously, in order to prevent the reflected sound from being produced at the second auricular attachment member 23B due to changes caused in acoustic impedance characteristics by sudden changes in the inside diameter and the cross-sectional area.

Although not shown, a third auricular attachment member for a person whose external acoustic meatus A has an inside tube 21 may be so arranged that, conversely to that shown in FIG. 14, it is gradually increased in diameter from the auricular attachment section to the entrance C to the external acoustic meatus A towards the fitting section 23*b* to the acoustic tube 21.

If the auricular attachment member 23 is made detachable, and several such members of different sizes are commutatingly used to suit the inside diameter $W_0$ of the external acoustic meatus A of the particular user, the sound reproducing apparatus may be rendered universal since only one type of acoustic tube 21 having a predetermined inside diameter sufficies to suit the inside diameters $W_0$ of the external acoustic meatus A of all users.

Also the difference between the inside diameter $W_0$ of the external acoustic meatus A and the inside diameter W of the acoustic tube 21 may be compensated by the auricular attachment member 23, and the acoustic impedance characteristics may be prevented from being changed when the sound reflected from the tympanic membrane 8 is introduced from the external acoustic meatus A into the acoustic tube 21 to prevent the reflected sound from being produced.

In any of the acoustic tubes employed in the above described illustrative embodiments, the sound reflected from the external acoustic meatus of the auricle is attenuated within the acoustic tube to prevent the sound from being radiated out of the tube, as well as to prevent the reflected sound from being reflected back at the other end of the tube towards the auricle. That is, the other end of the acoustic tube is exempt from reflection by causing the reflected sound from the external acoustic meatus of the auricle to be attenuated within the acoustic tube. However, in order for the reflected sound to be attenuated in the acoustic tube which is no more than a void meatus, it becomes necessary to use an extremely long acoustic tube.

The embodiment of the sound reproducing apparatus explained hereinbelow, allows the length of the acoustic tube to be reduced in order to increase the attenuation of the reproduced sound from the speaker unit reflected from the auricle to realize the reduction in size of the sound reproducing apparatus.

Figure 15:
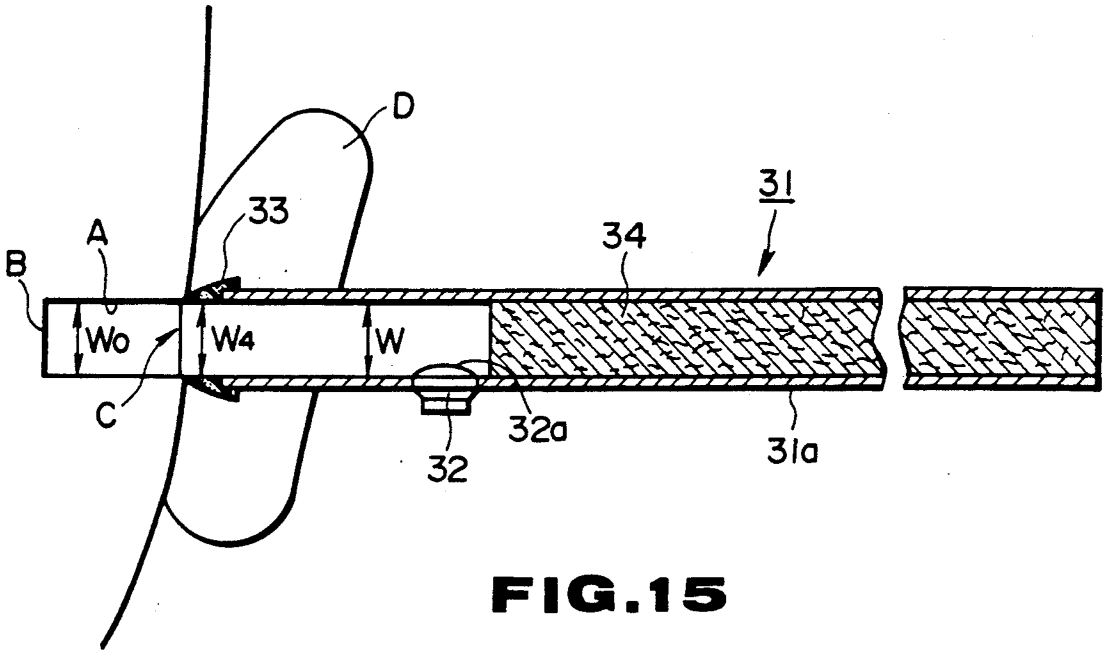
FIG. 15 is a cross-sectional view of a sound reproducing apparatus in which an acoustic resistance member is provided within the acoustic tube.

First, the sound reproducing apparatus shown in FIG. 15 is provided with an acoustic tube 31 formed as a tubular member having an inside diameter W which is uniform along its overall length and which is approximately equal to the inside diameter $W_0$ of the external acoustic meatus A of the auricle.

A speaker unit 32 is mounted to one side of the acoustic tube 31. This speaker unit is mounted to the acoustic tube 31 with its sound radiating surface 32a facing toward the interior of the tube 31. Preferably, the speaker unit 32 is mounted in such a manner as not to prevent the inside diameter W of the acoustic tube 21 from disturbing the acoustic impedance of the acoustic tube 31. An auricular attachment member 33 attached to the entrance C to the external acoustic meatus A of the auricle D is mounted to one end of the acoustic tube 31. Meanwhile, the auricular attachment member 33 also has its inside diameter $W_4$ approximately equal to the inside diameter W of the acoustic tube 31 so as to not change the acoustic impedance characteristics within the acoustic tube 31.

From the mounting position of the loudspeaker unit 32 within the acoustic tube 31 towards a portion 31a of the outer end of the tube 31, the inside of the tube is packed with an acoustic resistance member 34 for attenuating the sound radiated from the speaker unit 32 and which is reflected from the tympanic membrane B of the auricle D. As the acoustic resistance material 34, there are employed materials exhibiting conspicuous sound absorbing properties, such as wool, cotton or expanded urethane foam. By providing the acoustic resistance material 34 within the acoustic tube 31, the reflected sound from the auricle may be absorbed and attenuated in the inside of the acoustic tube 31 to reduce the length of the tube 31.

If the reflected sound can be attenuated completely in the inside of the acoustic tube 31 by the acoustic resistance member 34, the tube may have its other end opened or stopped, as desired.

Instead of providing only one kind of acoustic resistance member, several kinds of acoustic resistance members having different sound absorbing functions may be provided in the acoustic tube 31.

Figure 16:
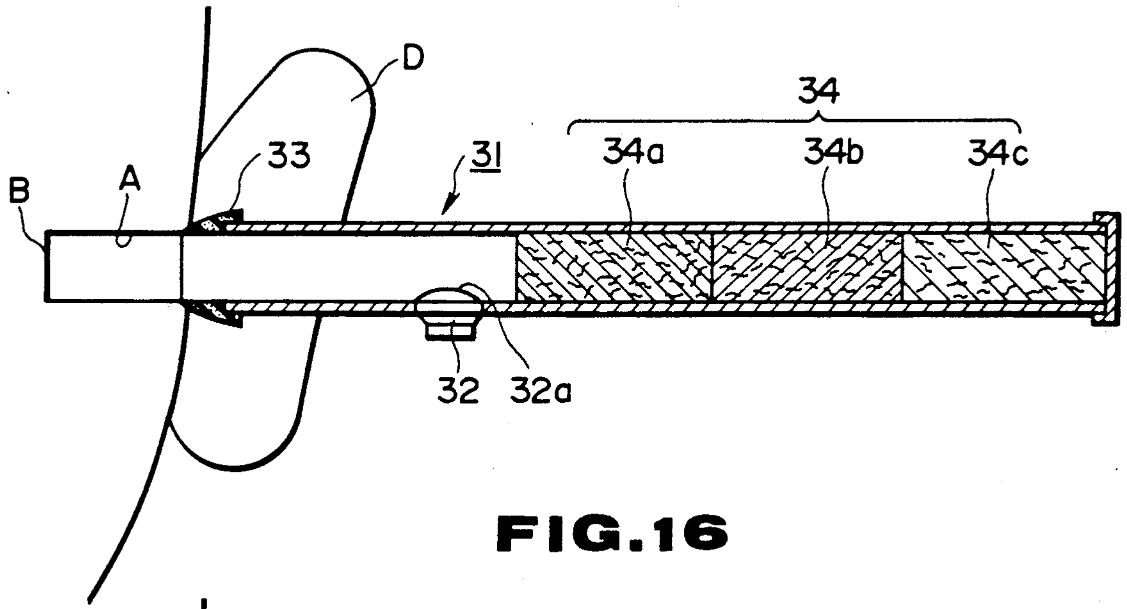
FIG. 16 is an enlarged cross-sectional view of a sound reproducing apparatus showing another example of the acoustic resistance member provided within the acoustic tube.

For example, as shown in FIG. 16, the acoustic resistance member 34 may be formed by a first acoustic resistance member 34a for effectively attenuating the low frequency range sound component, a second acoustic resistance member 34b for effectively attenuating the medium frequency range sound component and a third acoustic resistance member 34c for effectively attenuating the high frequency range sound component. These members are stacked one on the other in this sequence as viewed from the loudspeaker unit 32. The sound resistance member 34 arranged in this manner allows for attenuation of the reflected sound effectively and promptly over a wide frequency range.

The material of the acoustic resistance member 34 is not limited to the above described sound absorbing type material, as long as it is a resistance to and can attenuate the reflected sound. Thus, for example, it may be formed by a mesh of wool or wire affixed to the inner periphery of the acoustic tube 1.

Alternatively, the acoustic tube 31 itself may have the function of the acoustic resistance member.

Figure 17:
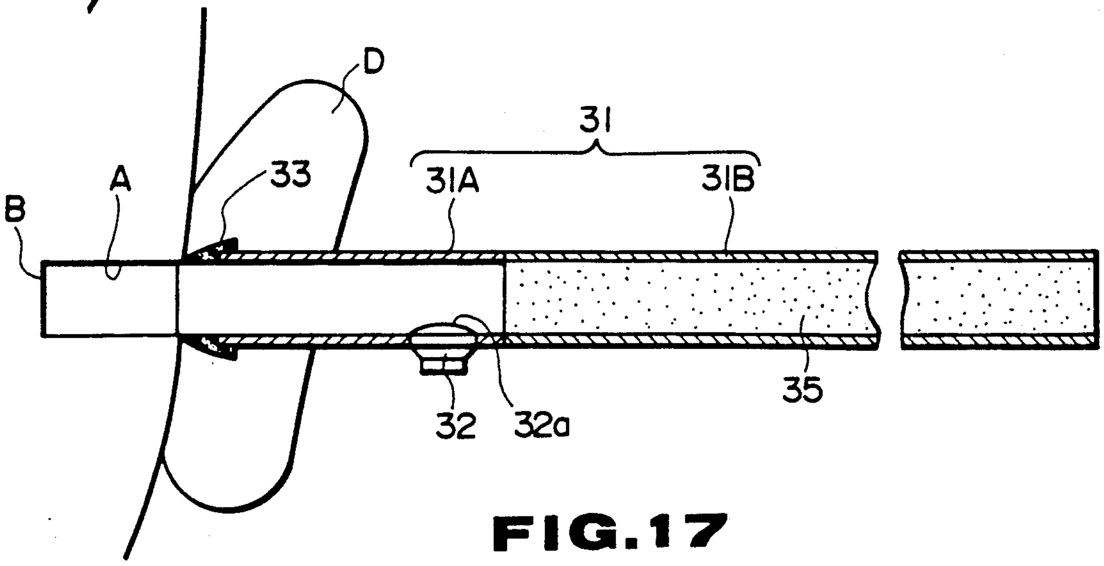
FIG. 17 is a cross-sectional view showing a sound reproducing apparatus in which the acoustic resistance section is formed on the inner surface of the acoustic tube.

Thus, as shown in FIG. 17, the acoustic tube 31 is made up of a reproduced sound take-out acoustic tube 31A, with the loudspeaker unit 32, and is adapted to transmit the reproduced sound radiated from the loudspeaker unit 32 to the auricle; and also of a reflected sound attenuating acoustic tube 31B which is connected to the end of this reproduced sound take-out acoustic tube 31A. This reflected sound attenuating acoustic tube 31B is designed to have the function of the acoustic resistance. In order for the acoustic tube to have such a function, the inner surface of the attenuating acoustic tube 31B is processed to increase air friction or resistance. For such processing, minute projections and recesses 35 may be formed on the inner periphery of the attenuating acoustic tube 31B, as shown in FIG. 17, by way of a so-called ration or matte finish.

Although not shown, an acoustic resistance member 34 may be provided within the attenuating acoustic tube 31B to promote attenuation of the reflected sound as well as to shorter further the length of the acoustic tube 31.

In the above described sound reproducing apparatus, when the acoustic tube 31 is seen from the external acoustic meatus A, the other end of the acoustic tube 31 is terminated by an acoustic impedance which is equivalent to the acoustic impedance of the external acoustic meatus A, so that, as a principle, no reflection may occur at the terminal end of the tube. Even though the sound reflection occurs at the other end of the acoustic tube 31, the reflected sound may be attenuated completely before arriving at the tympanic membrane B.

Therefore, for the sound reflected by the tympanic membrane B cannot be reflected again at the acoustic tube 31 and directed back towards the tympanic membrane B and thus the phenomenon of the sound image remaining stationary within the head of a listener during listening to the reproduced sound is prevented.

In the above described sound reproducing apparatus, the acoustic tube has a uniform diameter throughout from its one side towards its other side. However, in order to attenuate effectively the reflected sound within the acoustic tube, the acoustic tube may be constructed as explained hereafter.

Figure 18:
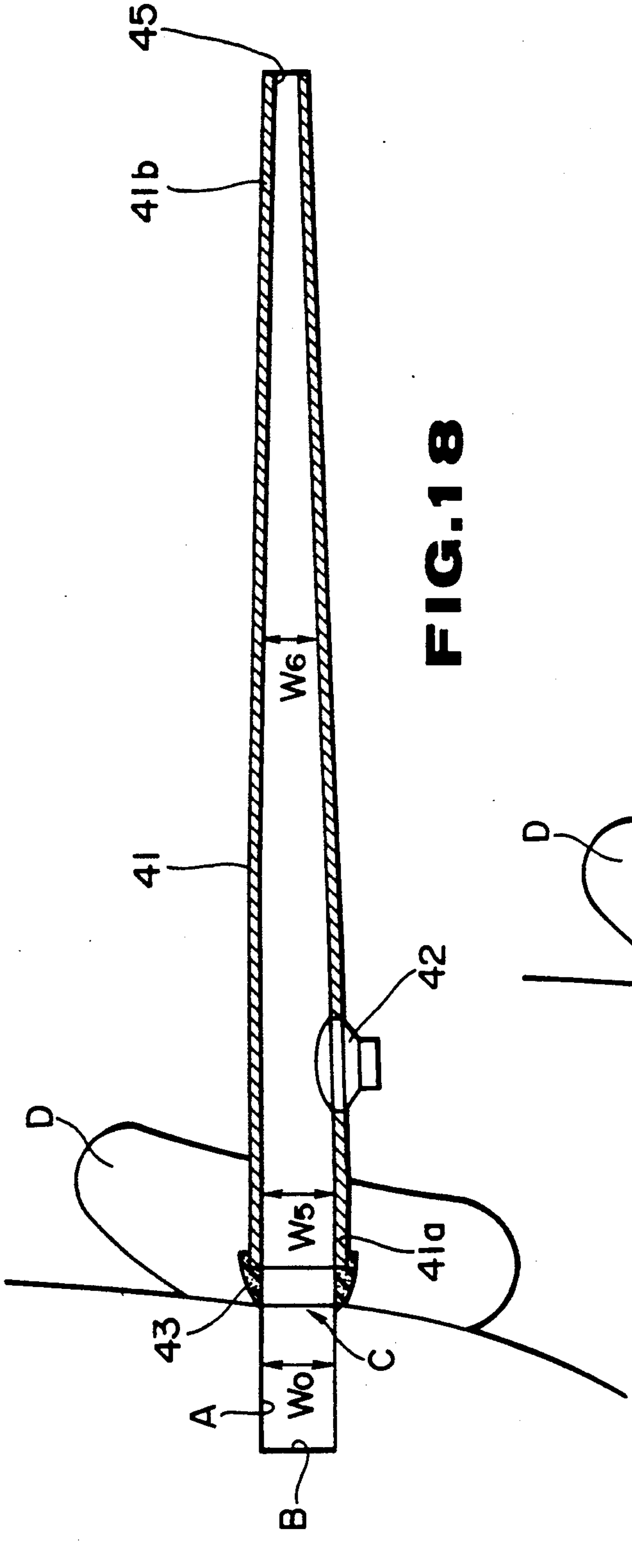
FIG. 18 is a cross-sectional view showing a sound reproducing apparatus provided with an acoustic tube having its inside diameter changed from its one end towards its other end.

The sound reproducing apparatus shown in FIG. 18 is provided with an acoustic tube 41 the inside diameter of which is changed gradually and continuously from its one side fitted with an auricular attachment member 43 towards its other side. This acoustic tube 41 has the inside diameter $W_5$ at its one end 41*a* approximately equal to the inside diameter $W_0$ of the external acoustic meatus A. The auricular attachment member 43 for enabling the acoustic tube 41 to be attached to the entrance C to the external acoustic tube 41 is fitted at the end 41*a* of the tube 41. Meanwhile, the attachment member 43 also has the inside diameter equal to the inside diameter $W_0$ of the external acoustic meatus A.

Meanwhile, the other end 41*b* of the acoustic tube 41 is arranged as explained hereafter so as to function as the non-sound-reflecting end.

That is, the inside diameter $W_6$ of the acoustic tube 41 is changed gradually and continuously from the attachment position of the speaker unit 42 to the tube 41 towards the other end 41*b* of the tube 41. In the present illustrative embodiment, the inside diameter $W_6$ of the tube is adapted to be decreased gradually. The reason for reducing the inside diameter $W_6$ of the acoustic tube 41 in this manner gradually and continuously with respect to the inside diameter $W_0$ of the external acoustic meatus A is to promote gradually the attenuation of the reflected sound in the tube insofar as the acoustic impedance in the acoustic tube 41 is not rendered variable so as to extinguish the reflected sound promptly within the acoustic tube. That is, this acoustic tube 41 has its inside diameter or cross-sectional area decreased gradually and continuously from the attachment side to the acoustic meatus A at it one end 41*a* to the other end or non-sound reflecting end 41*b*, with the mounting position of the speaker unit 42 to the acoustic tube 41 as the boundary region. This increases the resistance to the sound amplitude in the tube as the reflected sound incident from the one end 41*a* is propagated towards its other end or non-sound-reflecting end 41*b*, for attenuating the reproduced sound and ultimately extinguish the reflected sound. It will be noted that if the cross-sectional area of the acoustic tube 41 is changed gradually, no changes are caused in the acoustic impedance in the acoustic tube 41, so that reflected sound waves are not produced.

Hence, in the above described acoustic tube 41, after the reproduced sound radiated from the speaker unit 42 is reflected by the tympanic membrane B to be again incident into the tube 41, the sound may be prevented from being reflected back towards the external acoustic meatus and may thus be attenuated within this acoustic tube 41.

Figure 19:
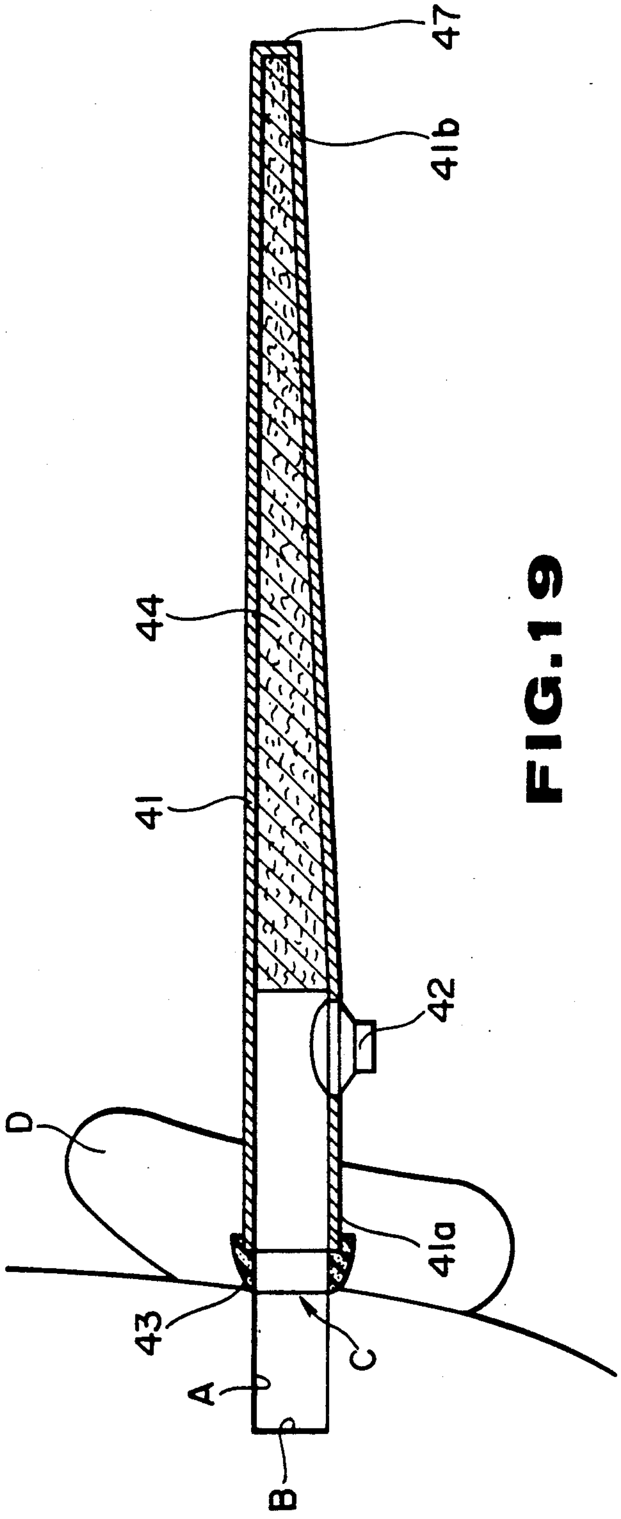
FIG. 19 is a cross-sectional view showing a sound reproducing apparatus in which an acoustic resistance member is provided within the acoustic tube having its inside diameter changed as in FIG. 18.

Meanwhile, when an acoustic resistance member 44, such as a sound absorbing material, is provided within the acoustic tube 41 in a region closer to the other end (the non-sound-reflecting end 41*b*) of the tube than is the speaker unit 42, attenuation of the reflected sound may be promoted further within the acoustic tube 41. It will be noted that, if the reflected sound may be attenuated completely within the acoustic tube 41 by the acoustic resistance member 44, the end face of the other end 41*b* of the tube 41 may be opened so at 46, as shown in FIG. 18, or closed as at 47, as shown in FIG. 19.

Meanwhile, the acoustic resistance member 44 provided within the tube 41 need not be formed by only one kind of the acoustic resistance material, but may be formed by a plurality of juxtaposed acoustic resistance members adapted for respectively attenuating the sounds of various frequency ranges.

The acoustic tube 41 itself may also be arranged as an acoustic resistance member. That is, the acoustic tube 41 presenting higher sound attenuation may be provided by having the inner wall surface of the acoustic tube 41 formed by minute indentations by way of a satin or matte finish, or by increasing air friction within the tube 41.

For further attenuating the sound and shortening the length of the acoustic tube 41, the acoustic resistance member 44, such as a sound absorbing material, may be provided within the acoustic tube 41 formed as the acoustic absorbing member as described hereinabove and thus providing high sound attenuation properties.

Figure 20:
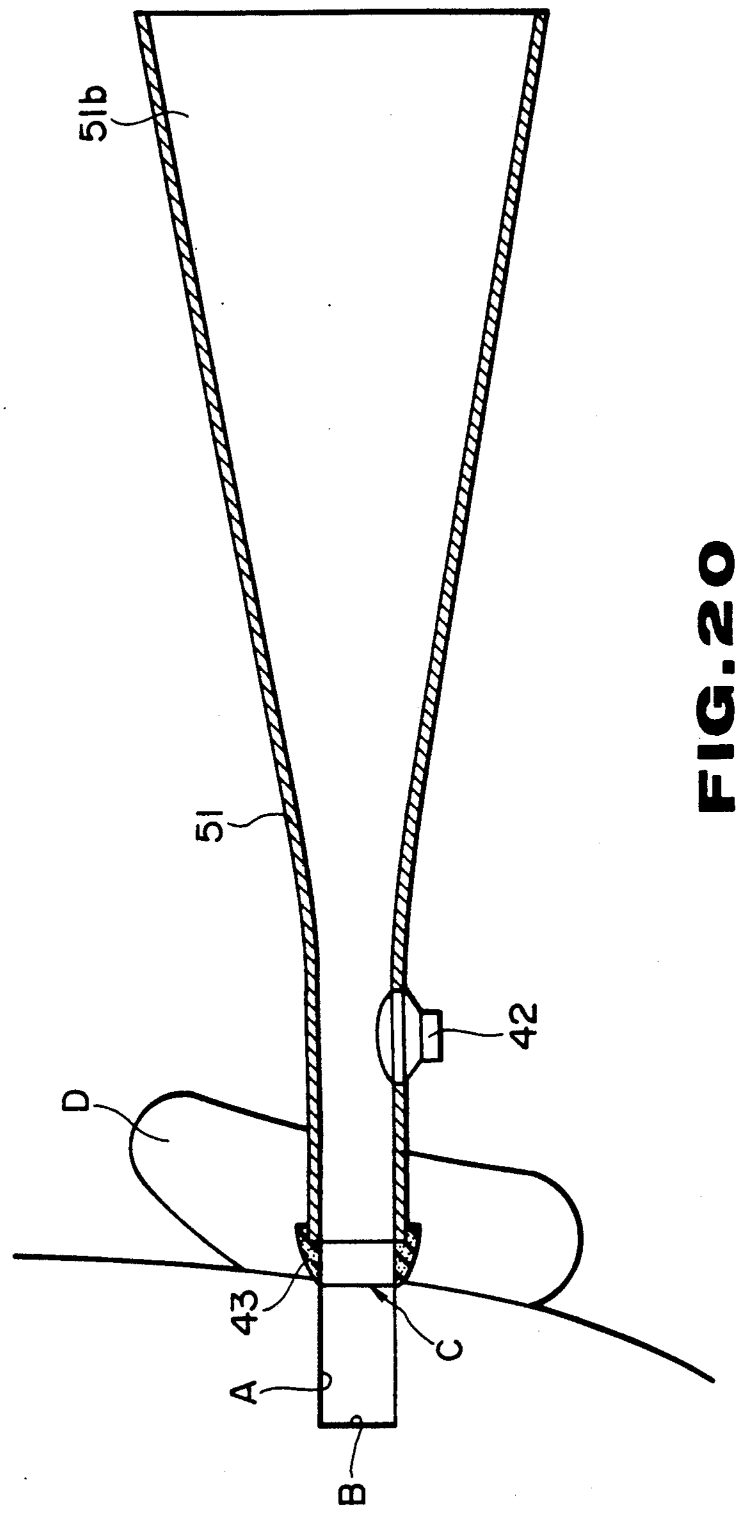
FIG. 20 is a cross-sectional view of a sound reproducing apparatus with an acoustic tube having its inside diameter increased gradually from its one end towards its other end.

FIG. 20 shows an acoustic tube 51 which is gradually and continuously increased in diameter towards the other end or non-sound-reflecting end 51*b*.

When the cross-sectional area of the acoustic tube 51 is increased in this manner gradually and continuously, the acoustic impedance within the acoustic tube 51 is not changed abruptly to prevent reflection of the reproduced sound from occurring. On the other hand, the acoustic impedance within the acoustic tube 51 can be assimilated quickly with that of the exterior side, resulting in prompt attenuation of the reproduced sound reflected from the tympanic membrane B.

Explained hereafter is an embodiment of the sound reproducing apparatus in which stereophonic sound reproduction is performed with the use of an acoustic tube which is fitted at one end with an auricular attachment section, and having at its end opposite to the auricular attachment section a non-sound-reflecting section.

The sound reproducing apparatus providing for such stereophonic sound reproduction is provided with an acoustic tube 61L for a left auricle $E_L$ and an acoustic tube 61R for a right auricle $E_R$. Each of the tubes 61L and 61R is an elongated tubular member having a uniform inside diameter $W_6$, and is opened at both ends. Each of the acoustic tubes 61L and 61R has an inside diameter $W_6$ approximately equal to the inside diameter $W_0$ of each of the left and right external acoustic meatus $e_L$ and $e_R$. The one open end of each of the acoustic tubes 61L and 61R is formed as a respective auricular attachment section 62L and 62R. These auricular attachment sections 62L, 62R are of reduced thickness at the foremost parts for insertion into and attachment to the entrances to the external acoustic meatus $e_L$, $e_R$, respectively.

That is, when the auricular attachment sections $62_L$,$62_R$ are attached in position to the external acoustic meatus $e_L$ and $e_R$ of the auricles $E_L$, $E_R$ respectively, the external acoustic meatuses $e_L$, $e_R$ and the acoustic tubes $61_L$, $61_R$ associated with the metuses $e_L$, $e_R$, respectively, are of approximately constant diameter and are continuous from the tympanic membranes $p_L$, $p_R$ to the other open ends $63_L$, $63_R$ of the acoustic tubes $61_L$, $61_R$.

On the peripheral surfaces of the acoustic tubes $61_L$, $61_R$, close to the auricular attachment sections $62_L$, $62_R$, there are bored a pair of speaker unit mounting through-holes $64_L$, $64_R$, functioning as speaker unit mounting sections. Speaker units $65_L$, $65_R$ for left and right ears are provided in these through-holes $64_L$, $64_R$ for closing them completely. These speaker units $65_L$, $65_R$ are formed as a dynamic type device including a magnetic yoke, a magnet forming a magnetic circuit, and a voice coil provided with a diaphragm, and are adapted to be displaced within a magnetic field formed by the magnetic field upon application of electric signals. These speaker units are disposed within the through-holes $64_L$, $64_R$, with their sound radiating sides facing to the inside of the acoustic tubes $61_L$, $61_R$, respectively.

The speaker units $65_L$, $65_R$ are mounted with their sound radiating surfaces substantially flush with the inner wall surfaces of the acoustic tubes $61_L$, $61_R$, respectively, so that the inside diameters of the acoustic tubes $61_L$, $61_R$ are constant and are not changed at the mounting sites of the speaker units $65_L$, $65_R$.

In the above described sound reproducing apparatus, the inside diameter remains substantially constant from the tympanic membranes $p_L$, $p_R$ to the opening ends $63_L$, $63_R$ of the acoustic tubes $61_L$, $61_R$ associated respectively with the tympanic membranes $p_L$, $p_R$, so that the acoustic impedance within the external acoustic meatuses $e_L$, $e_R$ is approximately equal to that within the associated acoustic tubes $61_L$, $61_R$, respectively.

For this reason, the reproduced sound radiated from the speaker units $65_L$, $65_R$ is not reflected when it is propagated through the inside of the associated acoustic tubes $61_L$, $61_R$ so as to be incident on the external acoustic meatuses $e_L$, $e_R$.

Also the sound propagated within the external acoustic meatuses $e_L$, $e_R$ as far as the tympanic membranes $p_L$, $p_R$ and reflected by these membranes $p_L$, $p_R$ is not reflected at the entrance to the external acoustic meatuses $e_L$, $e_R$ when it is propagated within the meatuses $e_L$, $e_R$ towards the associated acoustic tubes $61_L$, $61_R$.

The sound reflected from the tympanic membranes $p_L$, $p_R$ is propagated within the acoustic tubes $61_L$, $61_R$ towards the other opening ends $63_L$, $63_R$. The sound propagated within the acoustic tubes $61_L$, $61_R$ towards the opening ends $63_L$, $63_R$ is attenuated as it is propagated within the tubes $61_L$, $61_R$. The sound reaching the opening ends $63_L$, $63_R$ is reflected due to the changes in the acoustic impedance at the opening ends $63_L$, $63_R$ so as to be propagated back towards the auricular attachment sections $62_L$, $62_R$. However, it is attenuated in the course of propagation without again reaching the tympanic membranes $p_L$, $p_R$. That is, the ends of the acoustic tubes $61_L$, $61_R$ opposite to the auricular attachment sections $62_L$, $62_R$ and beyond the speaker units $65_L$, $65_R$ are arranged as the non-sound-reflecting sections.

In the above described sound reproducing apparatus, the sound reaching the tympanic membranes $p_L$, $p_R$ and reflected thereat does not reach the tympanic membranes $p_L$, $p_R$ to prevent a so-called "fixed" or "oppressed" feeling.

Figure 21:
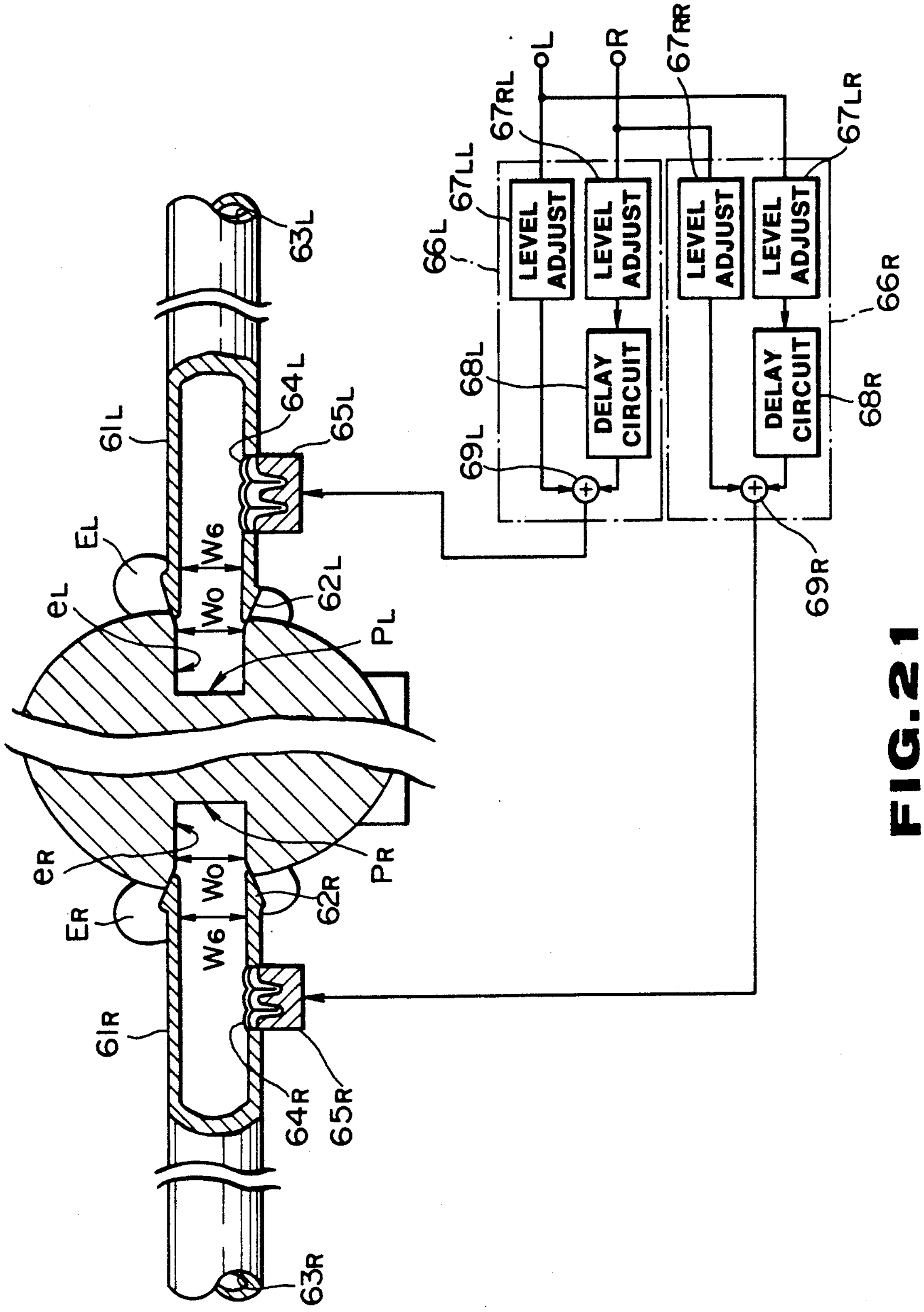
FIG. 21 is a cross-sectional view showing a sound reproducing apparatus adapted for stereophonic reproduction.

Referring to FIG. 21 showing a modified embodiment of the sound reproducing apparatus, electrical signals are supplied to the speaker unit $65_L$ for the left ear by way of a filter unit $66_L$ for left ear, and to the speaker unit $65_R$ for, right ear by way of a filter unit $66_R$ for the right ear.

In the filter unit for left ear $66_L$, electrical signals for the left ear supplied by way of a left channel input terminal L are transmitted by way of a first level adjustment circuit $67_{LL}$ to a first summation point $69_L$. On the other hand, electrical signals for the right ear supplied by way of a right channel input terminal R are transmitted by way of a second level adjustment circuit $67_{RL}$ and a first delay circuit $68_L$ to the first summation point $69_L$. The signals summed together by the first summation point $69_L$ are transmitted to the speaker unit for left ear $65_L$.

The right channel electrical signals are subjected to predetermined signal processing by the aforementioned second level adjustment circuit $67_{RL}$ and the first delay circuit $68_L$. This signal processing is performed so that the acoustic properties of the so-called cross-talk components will be imparted to the right channel electrical signals in order that the right channel sound from the right channel electrical signals, reproduced by the speaker unit and provided to the right side of the listener at some distance from the listener, may also be heard with the listener's left ear.

In the filter unit for right ear $66_R$, electrical signals for the right channel, supplied by way of a right channel input terminal R, are transmitted via a third level adjustment circuit $67_{RR}$, to a second summation point $69_R$. On the other hand, electrical signals for the right ear, supplied by way of a right channel input terminal R, are transmitted by way of a fourth level adjustment circuit $67_{LR}$ and a second delay circuit $68_R$ to the aforementioned second summation point $69_R$. The signals thus summed together at the second summation point $69_R$ are transmitted to the speaker unit for the right ear $65_R$.

The left channel electrical signals are subjected to predetermined signal processing by the aforementioned second level adjustment circuit $67_{LR}$ and the first delay circuit $68_R$. This signal processing is performed so that the acoustic properties of the so-called cross-talk components will be imparted to the left channel electrical signals.

The purpose of the first and third level adjustment circuits $67_{LL}$, $67_{RR}$ is to equilibrate the left and right channel electrical signals with respect to each other.

In the above described signal reproducing apparatus, the acoustic signals for the left channel and the acoustic signals for the right channel as cross-talk components are heard by the left ear, while the acoustic signals for the right channel and the acoustic signals for the left channel as cross-talk components are heard by the right ear.

Therefore, in the above described sound reproducing apparatus, the so-called "fixed" or "oppressed" feeling may be excluded, and the cross-talk components, are similar to those obtained when the sound is reproduced from a pair of loudspeaker units disposed at a distance from the listener, thus resulting in a satisfactory "relaxed" listening feeling.

Figure 22:
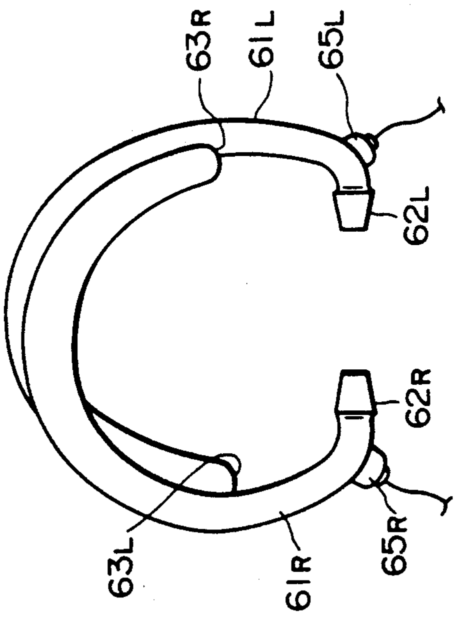
FIG. 22 is an overall perspective view of a sound reproducing apparatus adapted for stereophonic reproduction.

The acoustic tubes $61_L$, $61_R$ may be bent in advance to suit the contour of the listener's head, as shown in FIG. 22, in which case the bent portions of the acoustic tubes $61_L$, $61_R$ are designed so as to be constant in the inside diameter or in the cross-sectional area of the inner void space of the tubes. As a result, the tubes $61_L$, $61_R$ may exhibit a constant acoustic impedance from the tympanic membrane of the listener towards the opening ends $63_L$, $63_R$ thereof to prevent the reflected acoustic signals from the tympanic membranes from again reaching the tympanic membranes and thus to eliminate the aforementioned "fixed" or "oppressed" feeling.

If the acoustic tubes $61_L$, $61_R$ are superimposed one on the other and are interconnected at the respective outer peripheral sides, these tubes may be used as so-called head bands for attaching the sound reproducing apparatus to the listener's head.

Figure 23:
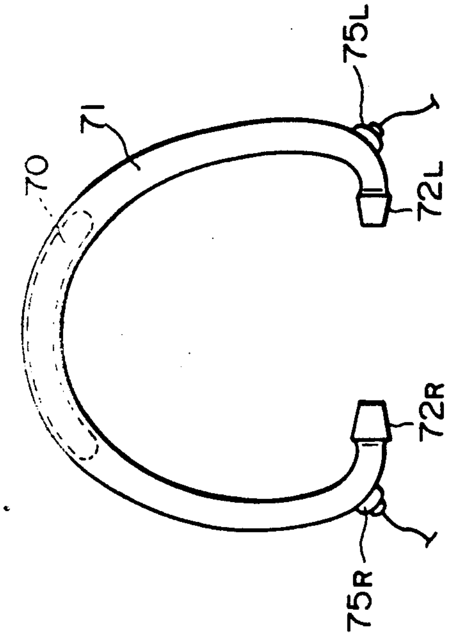
FIG. 23 is an overall perspective view of a sound reproducing apparatus adapted for stereophonic sound reproduction using only one acoustic tube.

FIG. 23 shows a modified embodiment of the sound reproducing apparatus making use of only one acoustic tube 71 which has been bent to conform to the shape of the listener's head. This acoustic tube 71 is a tubular member having a uniform inside diameter approximately equal to the inside diameter of the external acoustic meatus. Both open ends of the tube 71 are formed as a pair of auricular attachment sections 72$_R$, 72$_L$, and the speaker units 75$_R$, 75$_L$, associated with these auricular attachment sections 72$_R$, 72$_L$ are attached to the outer peripheral surfaces of the acoustic tube 71.

A sound absorbing member 70 is fitted in the inside of a central section, that is a section equidistant from the auricular attachment sections 72$_R$, 72$_L$, f the acoustic tube 71. The sound absorbing member 70 may be formed of a material having an increased surface area, such as fibers, including glass wool, or an expanded material, such as expanded styrene.

In the sound reproducing apparatus, shown in FIG. 23, the acoustic signal emanating from the speaker units 75$_L$, 75$_R$ will reach the respective tympanic membranes by way of the associated auricular attachment members 72$_L$, 72$_L$ and external acoustic meatuses. In the present sound reproducing apparatus, the acoustic impedance is set so as to be constant from the listener's tympanic membranes as far as the sound absorbing member 70. Thus the sound reflected at the tympanic membrane is incident into the acoustic tube 71$_B$ without reflection and is propagated within the tube 71 as it is attenuated before reaching the sound absorbing member 70. The reflected sound is absorbed in this sound absorbing member without being propagated towards the auricular attachment sections 72$_L$, 72$_R$. That is, the side of the acoustic tube 71 opposite to the speaker units 75$_L$, 75$_R$ and beyond the auricular attachment sections 72$_L$, 72$_R$ is formed as a non-sound-reflecting section. Thus, in the present embodiment, as in the case of the sound reproducing apparatus having a pair of acoustic tubes, as shown in FIG. 22 the sound reflected from the tympanic membrane does not again reach the tympanic membrane to eliminate the aforementioned "fixed" or "oppressed" feeling.

In the present embodiment, comprised of a single acoustic tube 71, the acoustic tube 63 may be employed as a so-called head band.

In the present embodiment comprised of a single acoustic tube 71, as shown in FIG. 23 the type of the material or the density may be changed or adjusted suitably so that the reproduced sound reaching the sound absorbing member 70 is allowed to pass through the sound absorbing member 70 after a predetermined attenuation.

In this case, the reproduced sound emanating from the speaker unit for left ear 75$_L$ reaches the left auricle, while it is simultaneously propagated within the acoustic tube 71 to reach the right auricle by way of the sound absorbing member 70. Similarly, the reproduced sound from the speaker unit for the right ear 75$_R$ reaches the right auricle, while it is simultaneously propagated within the acoustic tube 71 to reach the left auricle by way of the sound absorbing member 70. The reproduced sound reaching the auricles from the speaker units 75$_L$, 75$_R$ are attenuated and delayed by being conducted within the acoustic tube 71 and through the sound absorbing member 70. That is, the reproduced sound reaching the auricles from the speaker units 75$_L$, 95$_R$ exhibit the acoustic properties of the so-called cross-talk components, as mentioned hereinabove.

Therefore, in this case the acoustic signals of the cross-talk components, similar to those obtained when reproducing the sound from a pair of speaker units provided at a distance from a listener, may be produced without employing the aforementioned filter units, resulting in a satisfactory "relaxed" listening feeling.

Meanwhile, when the acoustic signals passing through the sound absorbing member 70 are used as the acoustic signals for the cross-talk components, the delay caused to these components is governed by such factors as the length of the acoustic tube 71 on the mounting positions of the speaker units 75$_L$, 75$_R$, while the amount of attenuation is governed by such factors as the length of the acoustic tube 71 or the type of the material or density of the sound absorbing member 70. Thus the acoustic signals for the cross talk components having the desired delay time and attenuation may be obtained by suitably changing or adjusting the length of the acoustic tube 71, mounting positions of the speaker unit 75$_L$, 75$_R$, or the type of the material or density of the sound absorbing member 70.

Meanwhile, there is proposed a binaural system of the head-attachment type sound reproducing apparatus adapted for stereophonic sound regeneration.

By the "binaural system" is meant such a system in which the left channel electrical signals are processed so as to exhibit acoustic properties of the so-called cross-talk components before being supplied to the right side speaker unit along with the right channel electrical signals, while the right channel electrical signals are processed so as to exhibit acoustic properties of the so-called cross-talk components before being supplied to the left channel speaker unit along with the left channel electrical signals. By the "acoustic properties of the cross-talk components" are meant such properties in which, when the left channel and right channel electrical signals are reproduced by left and right speaker units mounted at a distance from the listener, the left-channel sound or acoustic signals are heard with the right ear and the right-channel sound or acoustic signals are heard with the left ear.

Thus, in such a sound reproducing apparatus, the cross-talk components similar to those when the sound is reproduced from a pair of loudspeaker units provided at a distance from the listener are produced to realize the "relaxed" listening feeling.

The sound reproducing apparatus, explained hereunder, is of the above described binaural system.

The sound reproducing apparatus, explained hereafter, is of the above described binaural system.

Figure 24:
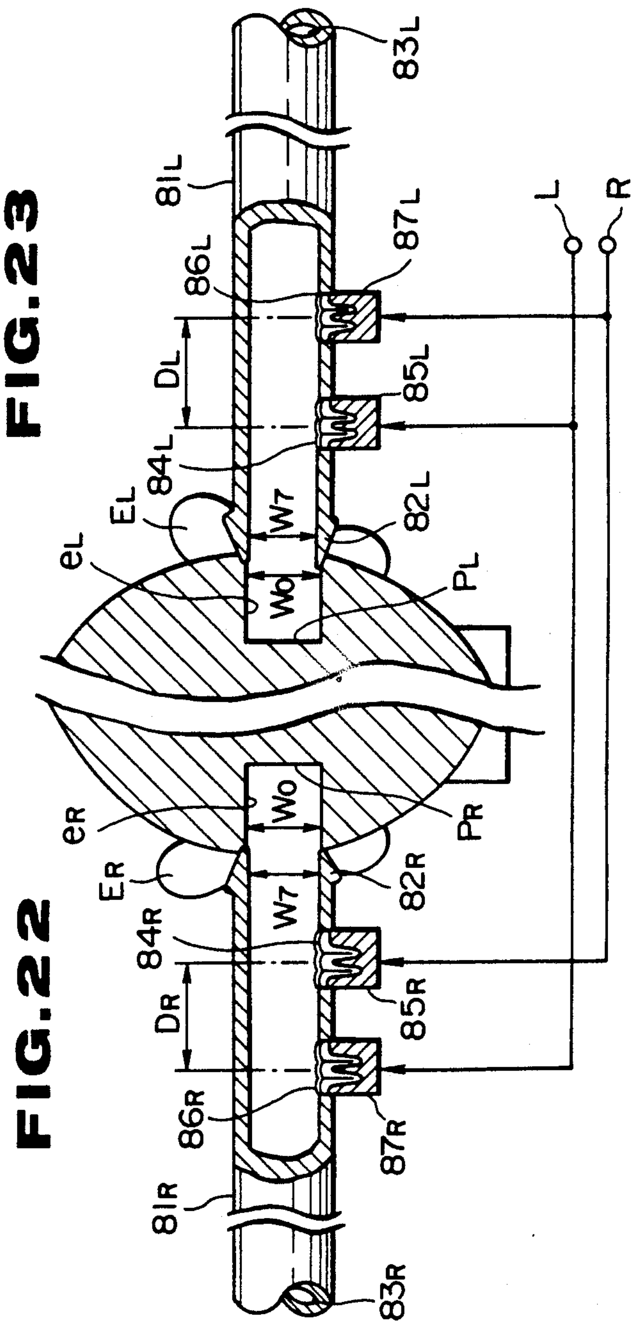
FIG. 24 is a cross-sectional view showing a sound reproducing apparatus adapted for binaural system stereophonic reproduction using a pair of loudspeaker units for each of the left and right channels.

Referring to FIG. 24, this sound reproducing apparatus has an acoustic tube 81$_L$ for a left auricle $E_L$ and an acoustic tube 81$_R$ for a right auricle 81$_R$. Each of the tubes 81$_L$ and 81$_R$ is an elongated tubular member having a uniform inside diameter $W_1$, and is opened at both ends. The inside diameter $W_1$ of each of these acoustic tubes 81$_L$, 81$_R$ is set so as to be approximately equal to the inside diameter $W_0$ of each of the meatuses $e_L$ $e_R$. The one open end each of the acoustic tubes 81$_L$, 81$_R$ is formed as a respective auricular attachment section 82$_L$, 82$_R$. These auricular attachment sections 82$_L$, 82$_R$ are of reduced thickness at the foremost parts to permit insertion and attachment of the foremost parts to the entrances of the external acoustic meatuses Thus, when the attachment sections $82_L$, $82_R$ are attached in positions to the external acoustic meatuses $e_L$, $e_R$ of the auricle $E_L$, $E_R$, the external acoustic meatuses $e_L$, $e_R$ and the associated acoustic tubes $81_L$, $81_R$ are continuous with respect to each other and are of an approximately constant diameter from the tympanic membranes $p_L$, $p_R$ as far as the opposite opening ends $83_L$, $83_R$ of the acoustic tubes $81_L$, $81_R$.

The mean inside diameter of the external acoustic meatus of a grown-up is about 7.5 mm, so that the inside diameter $W_7$ of the acoustic tubes $81_L$, $81_R$ is preferably selected to be approximately 6 to 9 mm.

On the peripheral surfaces of the acoustic tubes $81_L$, $81_R$, close to the auricular attachment sections $82_L$, $82_R$, there are formed loudspeaker unit mounting through-holes $84_L$, $84_R$, functioning as the mounting section for the first loudspeaker unit. Left and right first loudspeaker units $85_L$, $85_R$ are mounted in these left and right mounting through-holes $84_L$, $84_R$ for stopping up these through holes. These first loudspeaker units $85_L$, $85_R$ are designed for converting the electrical signals supplied thereto into corresponding acoustic signals, and are formed as a dynamic type speaker unit, comprised of, for example, a magnet and a magnetic yoke making up a magnetic circuit, and a voice coil fed with electrical signals and thereby displaced along with a diaphragm within a magnetic field defined by the magnetic circuit. These first loudspeaker units $85_L$, $85_R$ are mounted by the first through-holes $84_L$, $84_R$ with their sound radiating side facing to ward the interior of the acoustic tubes $81_L$, $81_R$.

On the peripheral surfaces of the acoustic tubes $81_L$, $81_R$, there are formed left and right second loudspeaker unit mounting through-holes $86_L$, $86_R$ , respectively. These second mounting through-holes $86_L$, $86_R$ are provided at positions further away from the auricular attachment sections $82_L$, $82_R$ than the first mounting through-holes $84_L$, $84_R$ by the distance $D_L$, $D_R$ shown in FIG. 24, respectively. The left and right second loudspeaker units $87_L$, $87_R$ are mounted in these left and right second loudspeaker unit mounting through-holes $86_L$, $86_R$ for stopping up these through-holes. These two second loudspeaker units $87_L$, $87_R$ are adapted for converting the electrical signals supplied thereto into acoustic signals, and are configured similarly to the first loudspeaker units. The second loudspeaker units $87_L$, $87_R$ are mounted via second loudspeaker mounting through-holes $86_L$, $86_R$ with the sound radiating surfaces facing to the interior of the acoustic tubes $81_L$, $81_R$.

Meanwhile, these two pairs of the loudspeaker units $85_L$, $85_R$, $87_L$, $87_R$ are mounted with the sound radiating surfaces substantially flush with the inner wall surfaces of the acoustic tubes $81_L$, $81_R$. For this reason, the acoustic tubes $81_L$, $81_R$ are of substantially uniform inside diameter even at mounting locations of the loudspeaker units $85_L$, $85_R$, $87_L$, $87_R$.

In the above described sound reproducing apparatus, the inside diameter remains substantially constant from the tympanic membranes $p_L$, $p_R$ as far as the opening ends $83_L$, $83_R$ of the acoustic tubes $81_L$, $81_R$ associated respectively with the tympanic membranes $p_L$, $p_R$, so that the acoustic impedance within the external acoustic meatuses $e_L$, $e_R$ is approximately equal to that within the associated acoustic tubes $81_L$, $81_R$, respectively.

For this reason, the reproduced sound radiated from the speaker units $85_L$, $85_R$ is not reflected when it is propagated through the inside of the associated acoustic tubes $81_L$, $81_R$ so as to be incident on the external acoustic meatuses $e_L$, $e_R$.

Also the sound propagated within the external acoustic meatuses $e_L$, $e_R$ as far as the tympanic membranes $p_L$, $p_R$ and reflected by the membranes $p_L$, $p_R$ is not reflected at the entrance to the external acoustic meatuses $e_L$, $e_R$ when it is propagated within the meatuses $e_L$, $e_R$ towards the associated acoustic tubes $81_L$, $81_R$.

The sound reflected from the tympanic membranes $p_L$, $p_R$ is propagated within the acoustic tubes $81_L$, $81_L$ towards the other opening ends $63_L$, $63_R$. The sound propagated within the acoustic tubes $81_L$, $81_R$ towards the opening ends $83_L$, $83_R$ is attenuated as it is propagated within the tubes $81_L$, $81_R$. The sound reaching the opening ends $83_L$, $83_R$ is reflected due to the changes in the acoustic impedance at the opening ends $83_L$, $83_R$ so as to be propagated back towards the auricular attachment sections $82_L$, $82_R$. However, it is attenuated in the course of propagation without again reaching the tympanic membranes $p_L$, $p_R$. That is, the ends of the acoustic tubes $81_L$, $81_R$ opposite to the auricular attachment sections $62_L$, $62_R$ and beyond the speaker units $85_L$, $85_R$ are arranged as the non-sound-reflecting sections.

In the sound reproducing apparatus shown in FIG. 24, left-channel electrical signals are supplied to the left-hand side first loudspeaker unit $85_L$ and the right-hand side second loudspeaker unit $87_R$ via left channel input terminal L, while right channel electrical signals are supplied to the right-hand side first loudspeaker unit $85_R$ and to the left-hand side second loudspeaker unit $87_L$ via right channel input terminal R.

Since the second loudspeaker units $87_L$, $87_R$ are spaced further apart from the auricular attachment sections $82_L$, $82_R$ than the first loudspeaker units $85_L$, $85_R$, the reproduced sound radiated from these second loudspeaker units $87_L$, $87_R$ reach the tympanic membranes $p_L$, $p_R$ with a predetermined time delay related with the sound velocity and the distance $D_L$, $D_R$ with respect to the reproduced sound radiated from the first loudspeaker units $85_L$, $85_R$. On the other hand, the acoustic signals radiated from the second loudspeaker units $87_L$, $87_R$ are propagated a longer distance than the reproduced sound radiated from the first loudspeaker units $85_L$, $85_R$ before reaching the tympanic membranes $p_L$, $p_R$, so that the reproduced sound radiated from these sound loudspeaker units $87_L$, $87_L$ are attenuated more markedly than those radiated from the first loudspeaker units $85_L$, $85_R$ when reaching the tympanic membranes $p_L$, $p_R$.

The acoustic characteristics of the reproduced sound radiated from the sound loudspeaker units $87_L$, $87_R$ and reaching the tympanic membranes $p_L$, $p_R$ with such delay and attenuation are closely approximate to the acoustic characteristics of the left-channel and right-channel reproduced sound heard by the right and left ears, respectively, in case of reproducing left- and right-channel electrical signals by left and right loudspeaker units provided at a distance from the hearer, that is, the acoustic characteristics of so-called cross-talk components.

In such a sound reproducing apparatus, the left-channel reproduced sound and the right-channel reproduced sound as the cross-talk component may be heard by the left ear, while the right-channel reproduced sound and the left channel reproduced sound as the cross-talk component may be heard by the right ear.

Therefore, in this sound reproducing apparatus, the acoustic signals of the cross-talk components are similar to those obtained when the sound is reproduced from a pair of loudspeaker units disposed at a distance from the listener, thus giving rise to a satisfactory "relaxed" listening feeling.

The attenuation and the time delay of the cross-talk components are governed by the distances $D_l$, $D_R$ between the left and right first loudspeaker units $85_L$, $85_R$ and the left and right second loudspeaker units $87_L$, $87_R$. Therefore, the acoustic signals of the cross-talk components having the desired delay time and attenuation may be obtained by suitably changing or adjusting the mounting positions of the loudspeaker units $85_L$, $85_R$, $87_L$, $87_R$.

It may occur that the difference in level between the reproduced sound radiated from the first loudspeaker units $85_L$, $85_R$ and the reproduced sound radiated from the second loudspeaker units, $87_L$, $87_R$ cannot be adjusted appropriately by the distances between the first loudspeaker units $85_L$, $85_R$ and the second loudspeaker units $87_L$, $87_R$. In such case, the level difference between the sounds reaching the tympanic membranes $p_L$, $p_R$ may be maintained at a desired value by employing loudspeaker units of different sensitivities as the left and right first loudspeaker units $85_L$, $85_R$ and the left and right second loudspeaker units $87_L$, $87_R$.

More specifically, in case of lower attenuation of the reproduced sound radiated from the second loudspeaker units $87_L$, $87_R$ and reaching the tympanic membranes $p_L$, $p_R$, the second loudspeaker units $87_L$, $87_R$ of lower sensitivities are employed. Conversely, in case the attenuation is high, the second loudspeaker units $87_L$, $87_R$ of higher sensitivities are employed.

Figure 25:
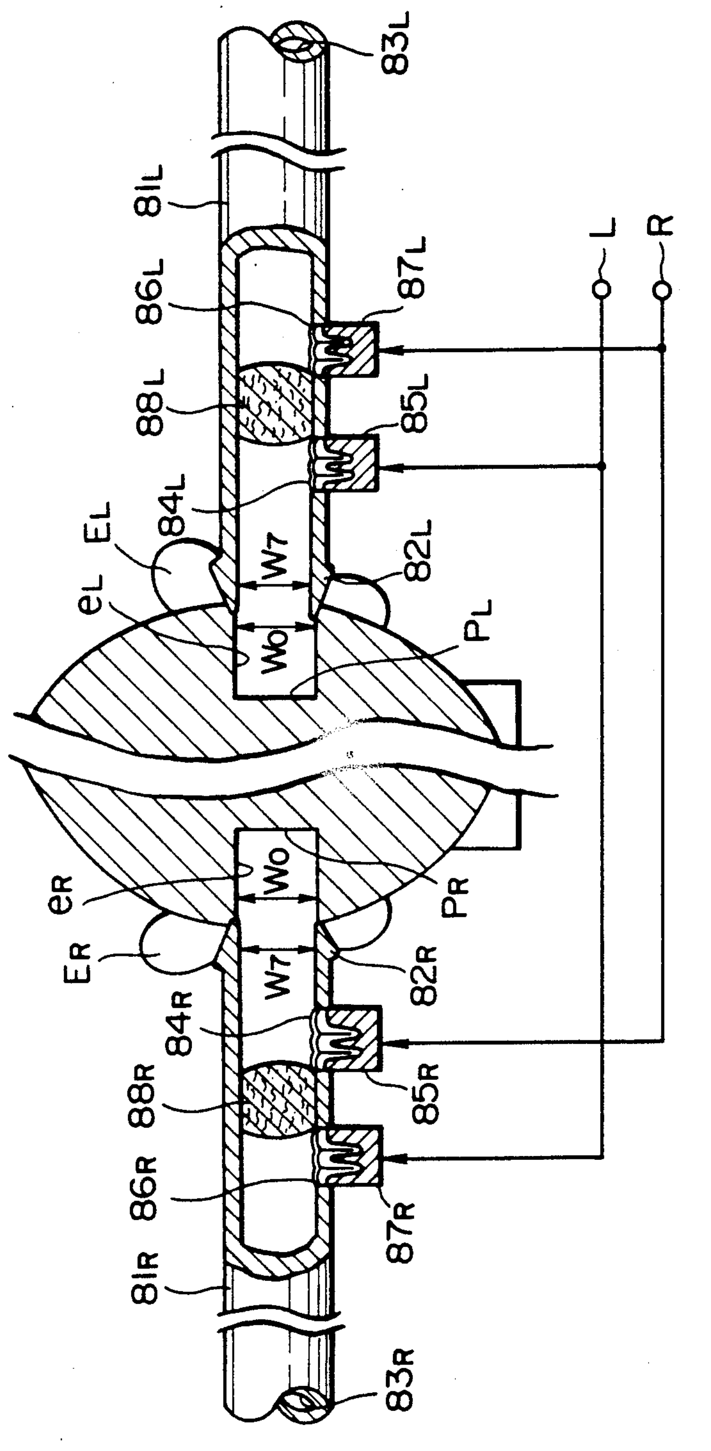
FIG. 25 is a cross-sectional view of a sound reproducing apparatus in which an acoustic resistance member is provided in a loudspeaker unit tube provided for each of the left and right channels.
Figure 26:
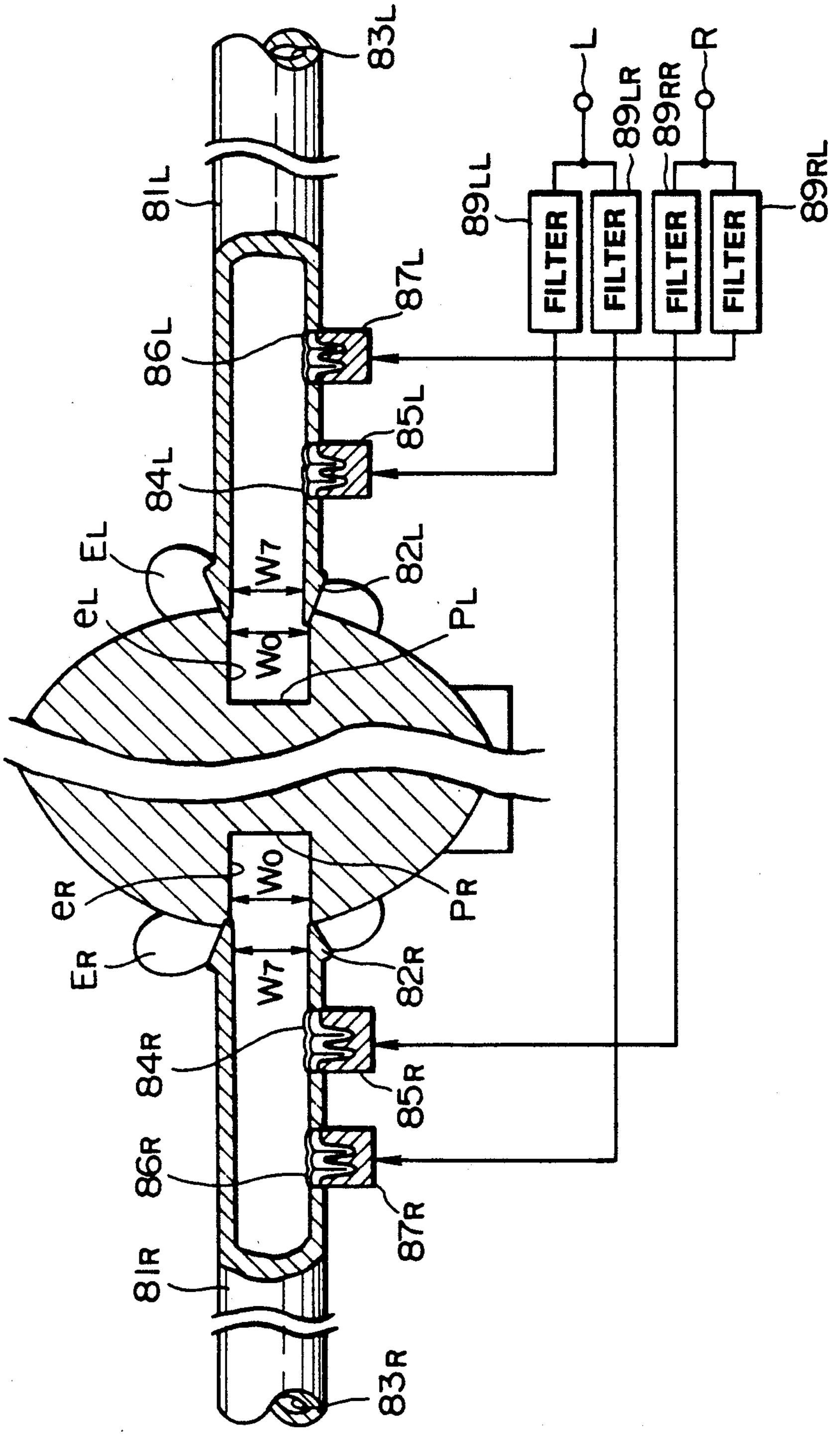
FIG. 26 is a cross-sectional view showing a sound reproducing apparatus adapted for binaural system stereophonic reproduction using a filter circuit.

In the above described sound reproducing apparatus, for adjusting the level difference between the reproduced sound radiated from the left and right first loudspeaker units $85_L$, $85_R$ and reaching the tympanic membranes $p_L$, $p_R$ and the reproduced sound radiated from the second loudspeaker units $87_L$, $87_R$, left and right sound absorbing members $88_L$, $88_R$ may be fitted in the interior of the acoustic tubes $81_L$, $81_R$, as shown in FIG. 25. This left hand side sound absorbing member $88_L$ is disposed within the interior of the left-hand side acoustic tube $81_L$ between the first loudspeaker unit $85_L$ and the second loudspeaker unit $87_L$, while the right hand side sound absorbing member $88_R$ is disposed within the interior of the right-hand side acoustic tube $81_R$ between the first loudspeaker unit $85_R$ and the second loudspeaker unit $87_R$.

The sound absorbing members $88_L$, $88_R$ may be those having increased surfaces, and thus formed of fibers, such as glass wool, or expanded materials such as expanded styrene. The materials or densities of the sound absorbing materials may be suitably changed or adjusted so that the reproduced sound reaching the sound absorbing members $88_L$, $88_R$ will pass therethrough after a predetermined sound attenuation. Thus the reproduced sound radiated from the left and right second loudspeaker units $87_L$, $87_R$ reach the auricles by way of the sound absorbing members $88_L$, $88_R$.

In this manner, the reproduced sound radiated from the second loudspeaker units $87_L$, $87_R$ and propagated within the acoustic tubes $81_L$, $81_R$ before reaching the auricles by way of the sound absorbing members $88_L$, $88_R$ are both attenuated and delayed.

Therefore, in the sound reproducing apparatus shown in FIG. 25, the reproduced sound radiated from the left and right second loudspeaker units $87_L$, $87_R$ exhibit acoustic properties of the crosstalk components similar to those when sound reproduction is performed by a pair of loudspeakers provided at a distance from the listener, thus assuring an excellent "relaxed" listening feeling.

In the above described sound reproducing apparatus, electrical signals may be supplied to the loudspeaker units $85_L$, $85_R$, $87_L$, $87_R$ by way of left and right first filter circuits $87_{LL}$, $89_{RR}$ and left and right second filter circuits $89_{RL}$, $89_{LR}$, respectively. More specifically, the left channel electrical signals are supplied from a left-channel input terminal L to the left-hand side first loudspeaker unit $85_L$ by way of a first filter circuit for right ear $89_{LL}$. The right channel electrical signals are supplied from a right channel input terminal R to the right-hand side first loudspeaker unit $85_R$ by way of a first filter circuit for the right ear $89_{RR}$, and the right channel electrical signals are also supplied from the right channel input terminal R to the left-hand side second loudspeaker unit $87_L$ by way of a second filter circuit for left ear $89_{RL}$. Finally, the right channel electrical signals are supplied from the right channel input terminal R by way of a first filter circuit for right ear $89_{RR}$.

The right channel electrical signals are subjected to predetermined processing, by the left-hand side second filter circuit $89_{RL}$, with respect to, for example, the signal level and the frequency response. This signal processing is performed in such a manner as to attenuate the signal level or the high frequency component or to provide the above mentioned acoustic characteristics of the so-called crosstalk components to the right channel electrical signals. Similarly, the left-channel electrical signals are subjected to predetermined processing by the right-hand side second level adjustment circuit $89_{LR}$. This signal processing is performed in such a manner as to provide the acoustic characteristics of the so-called crosstalk components to the left channel electrical signals.

Meanwhile, the first filter circuits $89_{LL}$, $89_{RR}$ are so designed that the left and right channel electrical signals supplied thereto undergo predetermined processing with respect to, for example, signal levels or frequency characteristics, in such a manner that the electrical signals passing through the second filter circuits $89_{RL}$, $89_{LR}$ will be used satisfactorily as the so-called crosstalk components.

In the above described sound reproducing apparatus, the "fixed" or "oppressed" listening feeling may be eliminated, at the same time that the crosstalk components similar to those obtained when sound reproduction is performed by a pair of loudspeaker units provided at a distance from the listener, thus giving rise to an optimum "relaxed" listening feeling.

It is noted that the loudspeaker unit employed in the sound reproducing apparatus of the present invention is not limited to the above described diaphragm type device, but the loudspeaker units of various types and constructions may be employed. So-called oscillators or shakers may also be employed.

Figure 27:
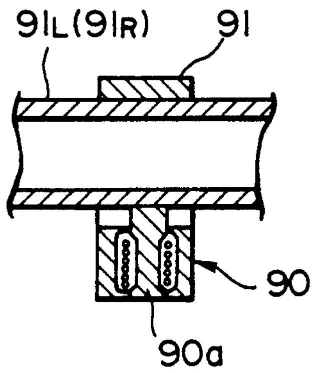
FIG. 27 is a cross-sectional view of a shaker provided at the output of the reproduced sound radiated into the acoustic tube in place of the loudspeaker unit.
Figure 28:
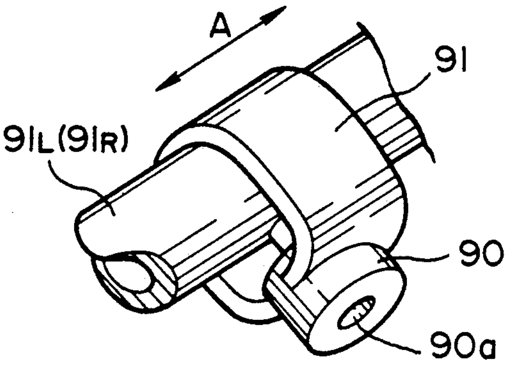
FIG. 28 is a perspective view showing an example of mounting the shaker to the acoustic tube.

More specifically, when using the shakers as the left and right first and second electrical-acoustic transducer elements, shakers 90 are mounted in position on the acoustic tubes $91_L$, $91_R$, as shown in FIGS. 27 and 28. These shakers 90 are each provided with axially movably supported shaker shafts 90*a*, which are excited into axial oscillations by, for example, electro-magnetic means, not shown.

These shakers 90 are mounted on the acoustic tube $91_L$ or $91_R$ by a holding member 91 so that the shaker shaft 90a is kept in pressure contact with the outer peripheral surface of each of the acoustic tubes. These acoustic tubes $91_L$, $91_R$ are free from mounting through-holes for mounting the shakers 90, and are formed as continuous tubular members of constant inside diameters.

When the shaker 90 is driven into oscillations, the oscillations of the shaker shaft 90a are transmitted via an outer wall of the acoustic tubes $91_L$ or $91_R$ so as to be propagated towards the inside of the acoustic tubes $91_L$ or $91_R$. In this manner, the acoustic signals may be propagated towards the inside of the acoustic tubes $91_L$ or $91_R$, as in the case of the above described loudspeaker units.

Meanwhile, the shakers 90 may be mounted on the acoustic tubes $81_L$, $81_R$ for adjustable axial sliding of the acoustic tubes, as indicated by an arrow mark A in FIG. 28. In such case, the distance between the shaker as the first electro-acoustic transducer element and the shaker as the second electro-acoustic transducer element may be adjusted freely so that the time delay of the acoustic signals of the so-called crosstalk components may be changed easily as desired.

In any of the above described embodiments, the sound reproducing apparatus is attached to the user's head with the auricular attachment sections at one end of the acoustic tubes in intimate contact with the entrances to the external acoustic meatuses. For this reason, when the user once wears such sound reproducing apparatus, the sound from outside can be scarcely heard. This represents a danger when, for example, the user is walking as he wears the apparatus at his ears.

In the embodiment of the sound reproducing apparatus described hereafter, the sound from outside can still be heard simultaneously with the reproduced sound, even when the external acoustic meatus is stopped up with the auricular attachment sections of the acoustic tubes.

Figure 29:
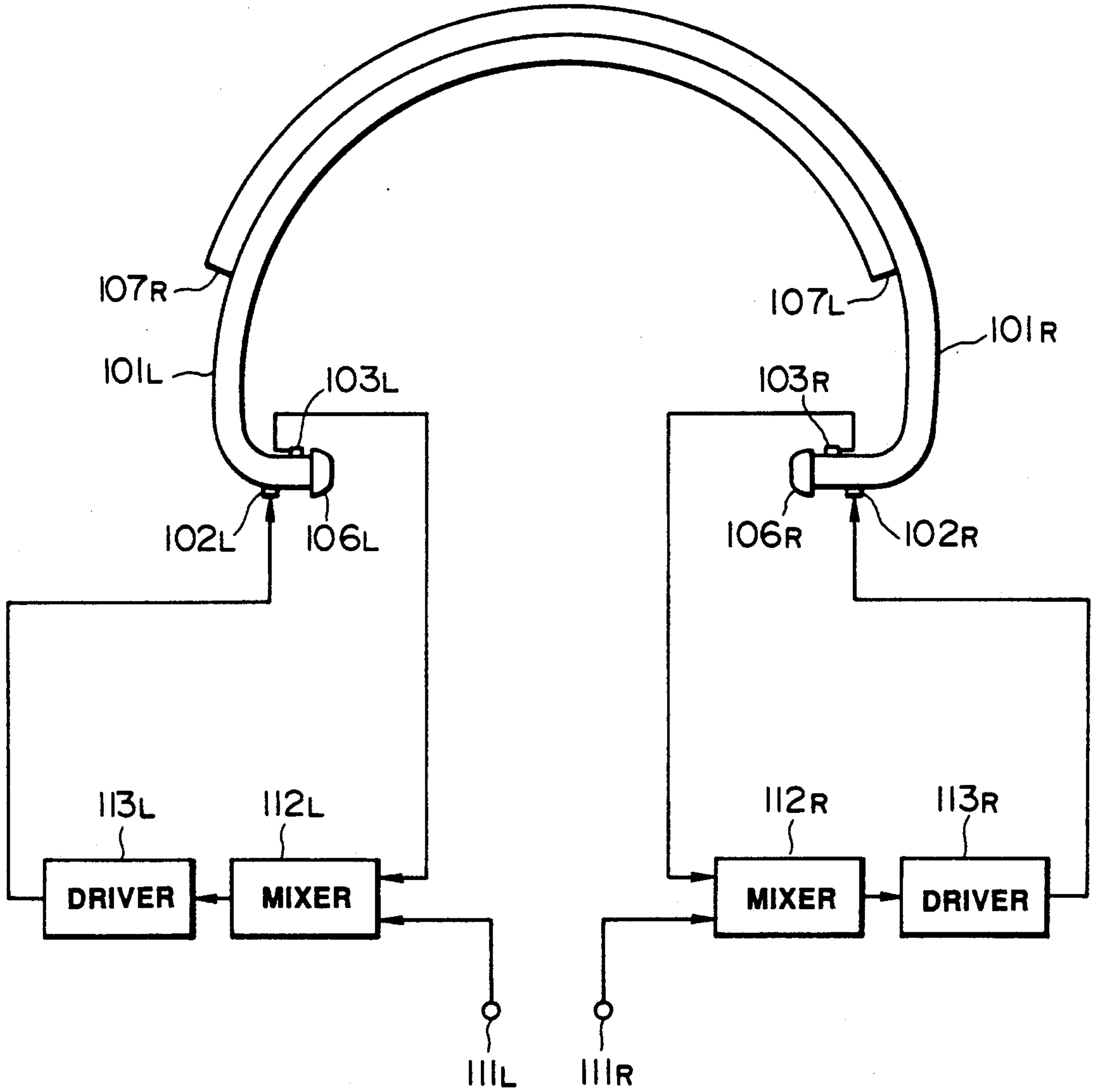
FIG. 29 is a front view showing a sound reproducing apparatus whereby the sounds from outside can be heard simultaneously with the reproduced sounds from the loudspeaker unit, and an electrical circuit thereof

Referring to FIG. 29, this sound reproducing apparatus is formed by acoustic tubes $101_R$, $101_L$, loudspeaker units $102_R$, $102_L$ and microphone units $103_R$, $103_L$ mounted to these acoustic tubes.

Each of the acoustic tubes $101_R$, $101_L$ has its inside diameter approximately equal to that of the external acoustic meatus A of an auricle D. The acoustic tubes $101_R$, $101_L$ are juxtaposed to each other and bent in the form of a user's head. By so doing, the length of each acoustic tube $101_R$, $101_L$ can be increased. Auricular attachment members $101_R$, $101_L$ are mounted to one ends $105_R$, $105_L$ of the acoustic tubes $101_R$, $101_L$, with the other ends $107_R$, $107_L$ of the tubes remaining open.

Figure 30:
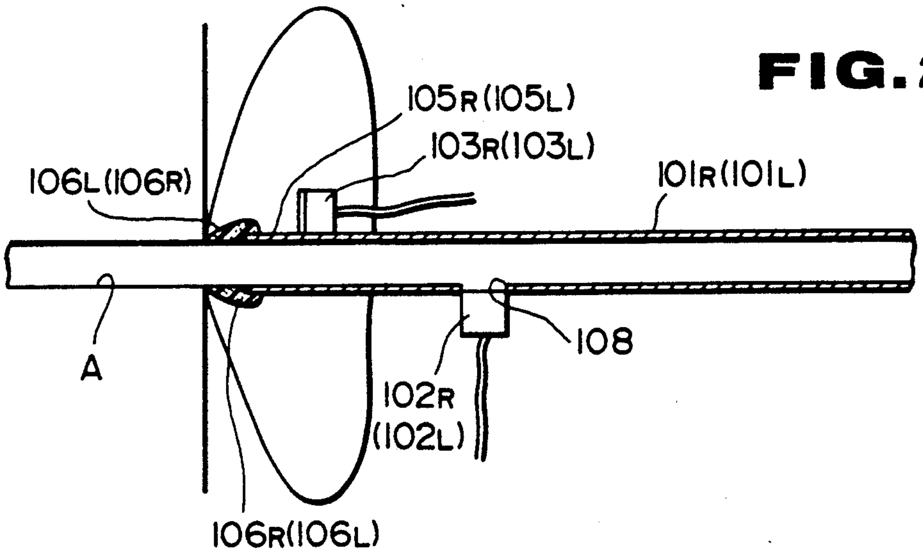
FIG. 30 is a cross-sectional view of a sound reproducing apparatus showing the state of mounting the microphone unit and the loudspeaker unit to the acoustic tube.

The loudspeaker units $102_R$, $102_L$ are mounted in the vicinity of the one ends $105_R$, $105_L$ of the acoustic tubes $101_R$, $101_L$, as shown in FIG. 30. More specifically, mounting through-holes 108 are formed in the vicinity of one ends $105_R$, $105_L$ of the acoustic tubes $101_R$, $101_L$ and the loudspeaker units $101_R$, $101_L$ are mounted in position in these through holes 108.

On the outer periphery of the acoustic tubes $101_R$, $101_L$, in the vicinity of one ends $105_R$, $105_L$ thereof, the microphone units $103_R$, $103_L$ are mounted, as shown in FIG. 30.

Figure 31:
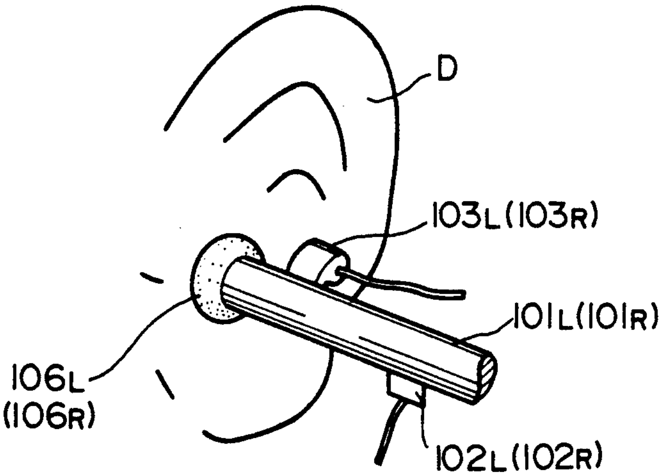
FIG. 31 is a perspective view of a sound reproducing apparatus fitted into entrances of external acoustic measures.

When the sound reproducing apparatus is in use, the auricular attachment members $106_R$, $106_L$ are fitted into the entrances C of the external acoustic meatures A, as shown in FIG. 31. When the sound reproducing apparatus is mounted in position in this manner, the microphone units $103_R$, $103_L$ are disposed in the vicinity of the user's ears. Thus the sounds from outside can be picked up at the microphone units $103_R$, $103_L$ at the same position as when these sounds are heard with ears.

In the above described sound reproducing apparatus, audio signals from a right-hand side input terminal $111_R$ and a left-hand side input terminal $111_L$ are supplied to mixers $112_R$, $112_L$, respectively. The outputs from the microphone units $103_R$, $103_R$ are supplied to the mixers $112_R$, $112_L$, respectively. The audio signals from the input terminal $111_R$, $111_L$ are mixed with the signals picked up by the microphone units $103_R$, $103_L$ in the mixers $112_R$, $112_L$, respectively. The outputs from the mixers $112_R$, $112_L$ are transmitted by way of drivers $113_R$, $113_L$ to the loudspeaker units $102_R$, $102_L$, respectively.

In this manner, mixed signals composed of the audio signals from the input terminals $111_R$, $111_L$ and the signals picked up by the microphone units $103_R$, $103_L$ are supplied to the loudspeaker units $102_R$, $102_L$. In this manner, the sounds from outside can be heard simultaneously with the audio signals from the input terminal $111_R$, $111_L$. The microphone units $103_R$, $103_L$ are disposed at the user's ears and, he or she can hear the sounds from outside at the same position as the ears. Hence the user can hear the sounds from outside as though he were hearing these sounds directly at his or her ears. On the other hand, since the microphone units $103_R$, $103_L$ are attached to the outer periphery of the acoustic tubes $101_R$, $101_L$ which are formed from a material exhibiting high sound barrier characteristics, there is no risk of howling even when the microphone units $103_R$, $103_L$ are mounted in close proximity to the loudspeaker units $102_R$, $102_L$.

The sound reproducing apparatus shown in FIG. 29 is so arranged and constructed that, by annexing the microphones to the acoustic tubes, the sounds from outside can be heard simultaneously with the reproduced sound, when the apparatus is worn by the user.

However, when the sounds from outside can be heard, it may occur that, there will be sources of noises, such as air conditioners, engines, or electric motors, which are extremely harsh to the ear, are also picked up by the microphones.

An embodiment of the sound reproducing apparatus, described hereafter, is so arranged that the usual sounds from outside can be heard and moreover the noise the outside can be eliminated.

The basic arrangement of the present illustrative embodiment is in common to that of the embodiment shown in FIG. 29 except for the following.

Figure 32:
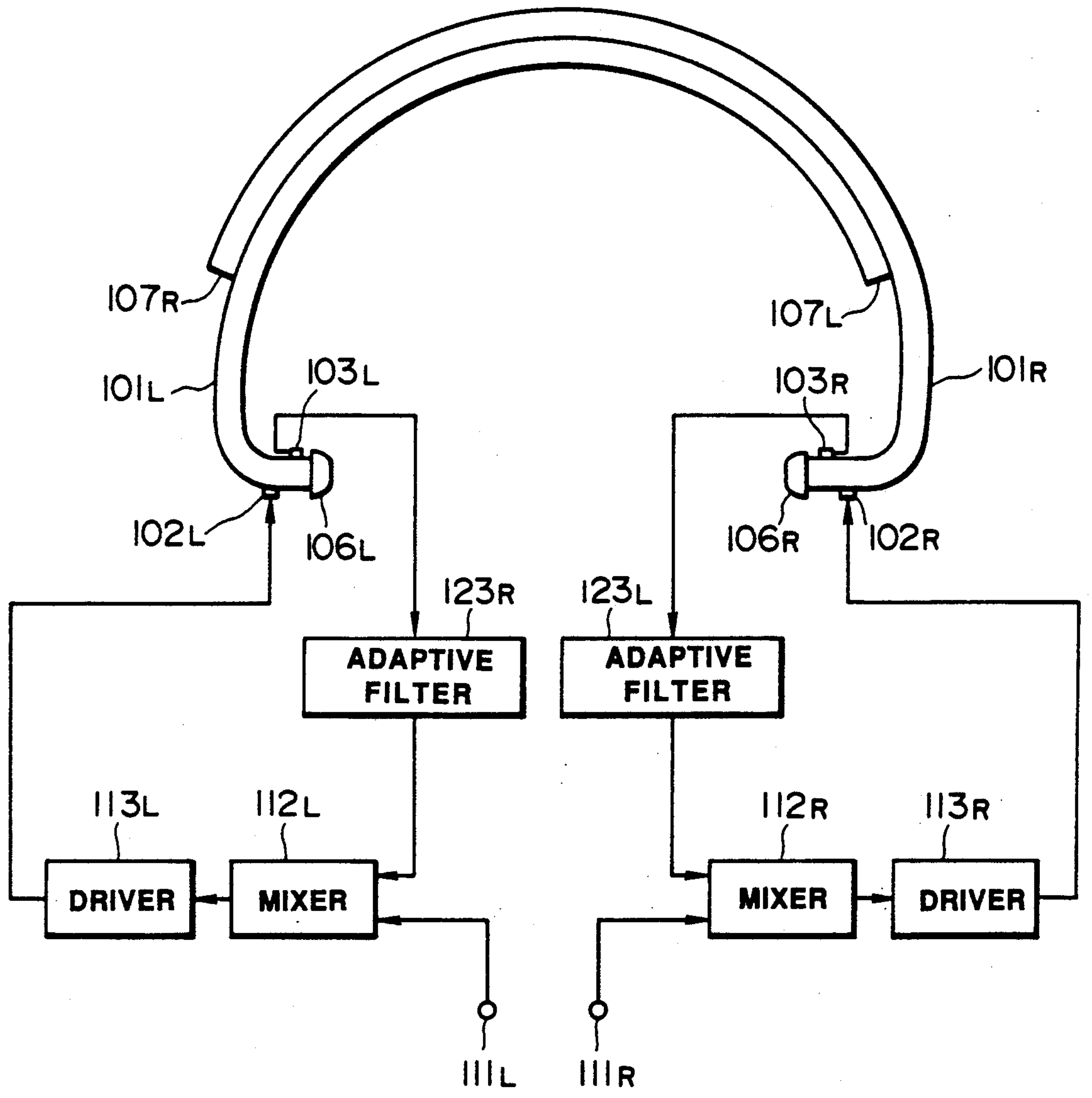
FIG. 32 is a front view showing a sound reproducing apparatus whereby the sounds from outside can be heard simultaneously with the reproduced sound by interrupting the exterior noises, and an electrical circuit thereof.

The sound reproducing apparatus, which allows elimination of the noises from the outside, and to hear the usual sounds from outside and the reproduced sound, is arranged as shown in FIG. 32. As shown therein, audio signals from an input terminal $111_R$ of right-hand side audio signals and an input terminal $111_L$ of left-hand side audio signals are supplied to mixers $112_R$, $112_L$, respectively. The outputs from a right side microphone unit $103_R$ and a left side microphone unit $103_L$ are supplied to mixers $112_R$, $112_L$ via adaptive filters $123_R$, $123_L$.

The adaptive filters $123_R$, $123_L$ are so arranged as to presume the time series data so as to minimize the errors of the minimum square method by a linear system and to eliminate periodic noise showing strong correlation. By these adaptive filters $123_R$, $123_L$, any noise components from outside that occur periodically, such as noises from electric motors or engines, are eliminated.

In the mixers $112_R$, $112_L$, the audio signals from the input terminals $111_R$, $111_L$ are mixed with output signals supplied from the microphone units $103_R$, $103_L$ via adaptive filters $123_R$, $123_L$. The outputs from the mixers $112_R$, $112_L$ are supplied via drivers $113_R$, $113_L$ to the right and left loudspeaker units $102_R$, $102_L$.

In this manner, the audio signals from the input terminals $111_R$ and $111_L$ are mixed with the signals picked up by the microphone units $102_R$, $102_L$ and the thus mixed signals are supplied to left and right loudspeaker units $102_R$, $102_L$. Thus the sounds from outside can be heard simultaneously with the audio signals from the input terminals $111_R$, $111_L$.

The signals from the left and right microphone units $103_R$, $103_L$ are passed through right and left adaptive filters $123_R$, $123_L$ and are thereby freed of noises exhibiting strong correlation. Hence, even when sources of noises, such as air conditioners, electric motors or engines exist in the near-by area, such noises cannot be heard.

In the above described sound reproducing apparatus, the noise components exhibiting strong correlation in the signals picked up by the right and left microphone units $103_R$, $103_L$ are removed by the right and left adaptive filters $123_R$, $123_L$. The sounds from outside, freed of noises by the adaptive filters $123_R$, $123_L$ and the audio signals from the input terminal $111_R$, $111_L$ are mixed together before being supplied to right and left loudspeaker units $102_R$, $102_L$. In this manner, the sounds from outside and the audio signals from the input terminals $111_R$, $111_L$ can be heard simultaneously. The signals picked up by the right and left microphone units $103_R$, $103_L$ are passed through the right and left adaptive filters, so that, even if there were noise sources, such as air conditioners, electric motors or engines, the S/N ratio is not deteriorated.

What is claimed is:

1. A sound reproducing apparatus, comprising:
   - an acoustic tube having first and second ends and having substantially a same inside diameter as that of an external acoustic meatus,
   - a loudspeaker unit mounted to said acoustic tube intermediate its first and second ends and such that a sound radiating surface thereof is directed to one side of said acoustic tube, and
   - said acoustic tube having its first end formed as an auricular attachment section and having its second end formed as a non-sound-reflecting end.

2. The sound reproducing apparatus according to claim 1, wherein said acoustic tube has an acoustic impedance approximately equal to an acoustic impedance of the external acoustic meatus.

3. The sound reproducing apparatus according to claim 1, wherein the second end of the acoustic tube is opened.

4. The sound reproducing apparatus according to claim 1, wherein said acoustic tube forms a part of means for attachment of the apparatus to a head of a user.

5. The sound reproducing apparatus according to claim 1, wherein said auricular attachment section is contoured to contact tightly with an entrance to the external acoustic meatus.

6. The sound reproducing apparatus according to claim 1, wherein said auricular attachment section has an inside diameter selected so as not to change an acoustic impedance of said acoustic tube.

7. The sound reproducing apparatus according to claim 6, wherein said auricular attachment section has an inside diameter approximately equal to the inside diameter of said acoustic tube.

8. The sound reproducing apparatus according to claim 7, wherein said auricular attachment section is formed of a resilient material.

9. The sound reproducing apparatus according to claim 8, wherein said auricular attachment section is detachably mounted to said acoustic tube.

10. The sound reproducing apparatus according to claim 1, wherein said acoustic tube has a region leading to the second end formed so as to increase an attenuation of reproduced sound from said loudspeaker unit reflected by a tympanic membrane of an ear of a user wearing the apparatus.

11. The sound reproducing apparatus according to claim 10, wherein said acoustic tube has its inside diameter changed gradually and continuously towards its second end.

12. The sound reproducing apparatus according to claim 10, wherein said acoustic tube has its inside diameter and an associated cross-sectional area of said inside diameter decreased gradually and continuously towards its second end.

13. The sound reproducing apparatus according to claim 12, wherein the acoustic tube has its second end closed and has an acoustic resistance provided within said acoustic tube.

14. The sound reproducing apparatus according to claim 10, wherein said acoustic tube has an inside diameter and an associated cross-sectional area of said inside diameter which decreases gradually and continuously towards its second end.

15. The sound reproducing apparatus according to claim 10, wherein said acoustic tube has at a region adjacent its second end an acoustic resistance means for increasing air friction in said acoustic tube.

16. The sound reproducing apparatus according to claim 1, wherein an acoustic resistance means is provided at a region adjacent to the second end of said acoustic tube for increasing an attenuation of reproduced sound from said loudspeaker unit reflected by a tympanic membrane of an ear of a user wearing the apparatus.

17. The sound reproducing apparatus according to claim 16, wherein said acoustic resistance means is formed by a plurality of acoustic resistance material means having different properties.

18. The sound reproducing apparatus according to claim 17, wherein said acoustic resistance materials comprise, from a side towards said loudspeaker unit, a first acoustic resistance material means for effectively decreasing a low frequency range sound component, a second acoustic resistance material means for effectively decreasing a mid frequency range sound component, and a third acoustic resistance material means for effectively decreasing a high frequency range sound component.

19. The sound reproducing apparatus according to claim 1, wherein said loudspeaker unit is mounted movably axially of said acoustic tube.

20. The sound reproducing apparatus according to claim 1, wherein said loudspeaker unit is formed by a piezoelectric element.

21. The sound reproducing apparatus according to claim 1, comprising a microphone unit provided on a lateral wall of said acoustic tube, said microphone unit having an output signal which is transmitted to said loudspeaker unit.

22. The sound reproducing apparatus according to claim 21, wherein said acoustic tube has a lateral side on which said microphone unit is provided so as to be closer to the auricle attachment section than said loudspeaker unit.

23. The sound reproducing apparatus according to claim 21, comprising noise eliminating means for eliminating noise components in the output signal from said microphone unit before supplying said output signal to said loudspeaker unit.

24. The sound reproducing apparatus according to claim 23, wherein said noise eliminating means is formed by a filter means having properties for eliminating noise components showing strong correlation.

25. The sound reproducing apparatus according to claim 24, comprising mixing means for mixing an output signal from said noise eliminating means and an acoustic signal supplied to said loudspeaker unit.

26. A sound reproducing apparatus, comprising:

acoustic tube means having a pair of auricular attachment means for respective attachment to left and right auricles of a user and having an inside diameter approximately equal to an inside diameter of each of a respective external acoustic meatus associated with the left and right auricles, left and right loudspeaker units provided on a peripheral surface of said acoustic tube means so that a sound radiating surface thereof faces toward an inside of said acoustic tube means, and said acoustic tube means having a portion thereof intermediate said auricular attachment means and said loudspeaker units formed as a non-sound-reflecting section.

27. The sound reproducing apparatus according to claim 26 wherein said acoustic tube means comprises a pair of acoustic tubes each fitted with one of said loudspeaker units.

28. The sound reproducing apparatus according to claim 26, wherein said acoustic tube means has an acoustic impedance approximately equal to an acoustic impedance of the external acoustic meatus.

29. The sound reproducing apparatus according to claim 27, wherein the other end of each of said acoustic tubes is open.

30. The sound reproducing apparatus according to claim 26, wherein said acoustic tube means forms at least part of attachment means for attaching the apparatus to a head of the user.

31. The sound reproducing apparatus according to claim 26, wherein each of said auricular attachment means is contoured to fit tightly with an entrance to the respective external acoustic meatus.

32. The sound reproducing apparatus according to claim 26, wherein each of said auricular attachment means has its inside diameter selected so as not to change an acoustic impedance of said acoustic tube means.

33. The sound reproducing apparatus according to claim 32 characterized in that each of said auricular attachment means has its inside diameter approximately equal to an inside diameter of said acoustic tube means.

34. The sound reproducing apparatus according to claim 26 further comprising signal processing means for adding cross-talk components to signals supplied to each of said respective loudspeaker units.

35. The sound reproducing apparatus according to claim 34, wherein said signal processing means supplies first channel acoustic signals and a lower level portion of second channel acoustic signals to the left loudspeaker units, and supplies second channel acoustic signals and a lower level portion of first channel acoustic signals to the right loudspeaker unit.

36. The sound reproducing apparatus according to claim 35, wherein the lower level portions of the first and second channel acoustic signals are each delayed for a predetermined time.

37. The sound reproducing apparatus according to claim 36, wherein said signal processing means comprises first and second level adjustment means for respectively adjusting the level of acoustic signals of the respective first and second channel, and first and second delay means for delaying respective output signals from said respective first and second level adjustment means for said predetermined time.

38. The sound reproducing apparatus according to claim 26, wherein the left loudspeaker unit receives acoustic signals of a first channel and the right loudspeaker unit receives acoustic signals of a second channel.

39. The sound reproducing apparatus according to claim 38, wherein a first additional loudspeaker unit is provided adjacent to and spaced a predetermined distance from the left loudspeaker unit and to which acoustic signals of the second channel are supplied and a second additional loudspeaker unit is provided adjacent to and spaced a predetermined distance from the right loudspeaker unit and to which acoustic signals of the first channel are supplied.

40. The sound reproducing apparatus according to claim 39, wherein acoustic signals of predetermined crosstalk components are obtained by adjusting the predetermined distance between the left or right loudspeaker unit respectively and the first or second additional loudspeakers, respectively.

41. The apparatus according to claim 26 wherein the acoustic tube means comprises a single acoustic tube.

42. A sound reproducing apparatus to be worn on a head of a user, comprising:

a substantially cylindrical acoustic tube having first and second ends and a substantially same inside diameter as that of an external acoustic meatus associated with an ear of the user;

a loudspeaker unit mounted to said acoustic tube intermediate its first and second ends and for directing a sound to the acoustic tube; and said acoustic tube having its first end formed as an auricular attachment for fitting to an entry region of the external acoustic meatus and having its second end formed as a non-sound-reflecting end, and wherein the acoustic tube has means for attachment to the head of the user.

43. The apparatus according to claim 42 wherein the means for attachment comprises the acoustic tube having a curvature adapted for at least partially wrapping around the head of the user.

44. The apparatus according to claim 42 wherein the loudspeaker unit is mounted closer to the first end than the second end of the acoustic tube.

45. The apparatus according to claim 42 wherein the loudspeaker unit directs sound waves toward a side wall of the acoustic tube and substantially in a direction perpendicular to a longitudinal extent of the tube.

46. The apparatus according to claim 42 wherein the loudspeaker unit is attached to a sidewall of the tube.

47. A sound reproducing apparatus, comprising:

acoustic tube means having a pair of auricular attachment means for respective attachment to left and right auricles associated with left and right ears of a user, the acoustic tube means and the auricular attachment means having an inside diameter approximately equal to an inside diameter of respective left and right external acoustic meatus associated with the left and right auricles of the ears of the user;

left and right loudspeaker units provided substantially at a peripheral surface of the acoustic tube means and spaced from the respective auricular attachment means so that a sound radiating surface thereof faces toward an inside of the acoustic tube means; and said acoustic tube means having means for preventing sound reflection at a portion thereof outwardly from the loudspeaker units and away from the respective auricular attachment means.

48. An apparatus according to claim 47 wherein said acoustic tube means comprises a single acoustic tube.

49. An apparatus according to claim 47 wherein said acoustic tube means comprises first and second acoustic tubes.

50. A sound reproducing apparatus, comprising:

an acoustic tube having substantially a same inside diameter as that of an external acoustic meatus;

a loudspeaker unit mounted to said acoustic tube so that a sound radiating surface thereof is directed to one side of said acoustic tube;

said acoustic tube having one end formed as an auricular attachment section and having another end formed as a non-sound-reflecting end; and the acoustic tube forming a part of means for attachment of the apparatus to a head of a user.

51. A sound reproducing apparatus, comprising:

an acoustic tube having substantially a same inside diameter as that of an external acoustic meatus;

a loudspeaker mounted to said acoustic tube so that a sound radiating surface thereof is directed to one side of said acoustic tube;

said acoustic tube having one end formed as an auricular attachment section and having another end formed as a non-sound-reflecting end; and said loudspeaker unit being mounted movably axially of said acoustic tube.

52. A sound reproducing apparatus, comprising:

an acoustic tube having substantially a same inside diameter as that of an external acoustic meatus;

a loudspeaker mounted to said acoustic tube so that a sound radiating surface thereof is directed to one side of said acoustic tube;

said acoustic tube having one end formed as an auricular attachment section and having another end formed as a non-sound-reflecting end; and a microphone unit being provided on a lateral wall of said acoustic tube, said microphone unit having an output signal which is transmitted to said loudspeaker unit.

53. A sound reproducing apparatus, comprising:

at least one acoustic tube having a pair of auricular attachment sections attached to left and right auricles and having an inside diameter approximately equal to an inside diameter of an external acoustic meatus;

left and right loudspeaker units provided on a peripheral surface of said acoustic tube so that a sound radiating surface thereof faces to an inside of the acoustic tube; and said acoustic tube having a portion thereof away from said auricular attachment sections and between said loudspeaker units formed as a non-sound-reflecting section.

* * * * *